United States Patent [19]

Cheng

[11] Patent Number: 6,077,834
[45] Date of Patent: *Jun. 20, 2000

[54] RECEPTOR LIGAND-FACILITATED DELIVERY OF BIOLOGICALLY ACTIVE MOLECULES

[76] Inventor: Pi-Wan Cheng, 15679 Webster St., Omaha, Nebr. 68118

[ * ] Notice: This patent issued on a continued prosecution application filed under 37 CFR 1.53(d), and is subject to the twenty year patent term provisions of 35 U.S.C. 154(a)(2).

[21] Appl. No.: 08/790,290

[22] Filed: Jan. 29, 1997

Related U.S. Application Data

[60] Provisional application No. 60/011,368, Feb. 9, 1996.

[51] Int. Cl.[7] .................................................. A61K 48/00
[52] U.S. Cl. .......................... 514/44; 424/450; 435/69.1; 435/320.1; 435/325; 435/455; 435/458
[58] Field of Search .............................. 424/450; 514/7.1, 514/9, 44; 435/69.1, 172.3, 325, 320.1, 455, 458; 935/52, 66, 32, 57

[56] References Cited

U.S. PATENT DOCUMENTS

| | | | |
|---|---|---|---|
| 4,897,355 | 1/1990 | Eppstein et al. | 435/325 |
| 5,264,618 | 11/1993 | Felgner et al. | |
| 5,279,833 | 1/1994 | Rose | 424/450 |
| 5,328,470 | 7/1994 | Nabel et al. | 604/101 |
| 5,334,761 | 8/1994 | Gebeyehu et al. | 564/197 |
| 5,451,661 | 9/1995 | Wan | 530/345 |
| 5,455,157 | 10/1995 | Hinzpeter et al. | 435/6 |
| 5,459,127 | 10/1995 | Felgner et al. | 514/7 |
| 5,547,932 | 8/1996 | Curiel et al. | 435/65 |
| 5,578,475 | 11/1996 | Jessee | 435/455 |
| 5,580,859 | 12/1996 | Felgnel et al. | 514/44 |
| 5,631,237 | 5/1997 | Dzau et al. | 514/44 |
| 5,635,380 | 6/1997 | Naftelan et al. | 435/455 |
| 5,681,571 | 10/1997 | Holmgren et al. | 435/236.1 |
| 5,736,392 | 4/1998 | Hawley-Nelson et al. | 435/320.1 |
| 5,780,052 | 7/1998 | Khaw et al. | 424/450 |
| 5,786,214 | 7/1998 | Holmberg | 435/375 |
| 5,827,703 | 10/1998 | Debs et al. | 435/455 |
| 5,837,533 | 11/1998 | Boutin | 435/320.1 |

FOREIGN PATENT DOCUMENTS

WO 95/17373   6/1995   WIPO.

OTHER PUBLICATIONS

Webster's II New Riverside University Dictionary (1994, pp. 132 and 299).

Coghlan, New Scientist, vol. 148, 14–15, 1995.

Mastrangelo et al., Seminars in Oncology, vol. 25, 1:4–21, 1996.

Gunzberg et al., Molecular Medicine Today, 1995, pp. 410–417.

Hong et al., Chinese Medical J., 108, 5, 332–337, 1995.

Wagner et al., P. N. A. S., vol. 89, 6099–6103, 1992.

Kolata, *New York Times*, Jul. 25, 1995, p. 3, C3, 1995.

Gao et al., J. of Liposome Res., 3, 1, 17–30, 1993.

Cheng, P.W., "Correction of the Chloride Transport Abnormality of CFT1 Cells by Transferrin–Facilitated Gene Transfer Mediated by Liposome", Abstract Submitted Sep. 8, 1995 for the Ninth Annual North American Cystic Fibrosis Conference, Dallas, Texas—Oct. 12–15, 1995.

Cheng, Pi–Wan, "Receptor Ligand–Facilitated Gene Transfer: Enhancement of Liposome–Mediated Gene Transfer and Expression by Transferrin", *Human Gene Therapy*, (Feb. 10, 1996) 7:275–282, Mary Ann Liebert, Inc.

*Primary Examiner*—Scott D. Priebe
*Assistant Examiner*—Dave Trong Nguyen
*Attorney, Agent, or Firm*—Zarley, McKee, Thomte, Voorhees & Sease

[57] ABSTRACT

Disclosed is a delivery system for biologically active molecules or agents which must enter cells to exert their effect. The delivery system comprises a mixture of cationic lipid in combination with a receptor ligand and is particularly suited for intracellular delivery of polynucleotides.

19 Claims, 15 Drawing Sheets

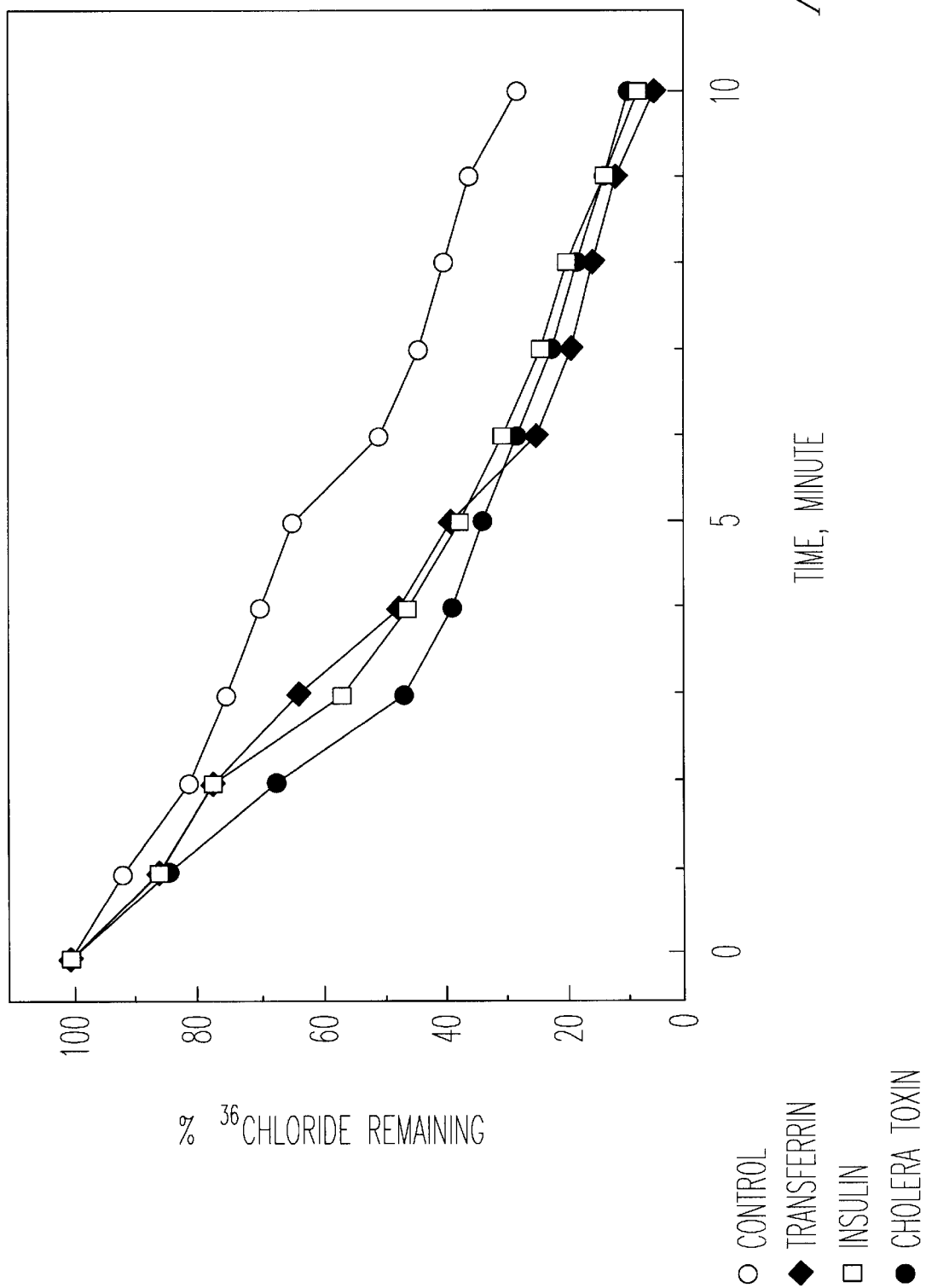

RECEPTOR LIGAND-FACILITATED DELIVERY OF BIOLOGICALLY ACTIVE MOLECULES

CROSS-REFERENCE TO RELATED APPLICATION

This application is based on United States Provisional Application Ser. No. 60/011,368 filed Feb. 9, 1996, entitled RECEPTOR LIGAND-FACILITATED GENE TRANSFER. Priority is claimed under 35 U.S.C. Section 119(e).

This invention was supported at least in part by a grant from the National Institutes of Health (HL48282). The United States Government has certain rights in this invention.

FIELD OF THE INVENTION

This invention is in the field of intracellular delivery of biologically active molecules.

BACKGROUND OF THE INVENTION

At the present time, major somatic gene transfer approaches employ either viral (Morgan, J. R., Tompkins, R. G., and Yarmuch, M. L. (1993), "Advances in recombinant retroviruses for gene delivery," Adv. Drug Del., Rev. 12, 143–158; Colledge, W. H. (1994), "Cystic fibrosis gene therapy." Curr. Opin. Gene Develop., 4, 466–471; Trapnell, B. C. and Gorziglia, M. (1994), "Gene therapy using adenoviral vectors," Curr. Opin. Biotechnol., 5, 617–625) or nonviral vectors (Cotten, M. and Wagner, E. (1993), "Non-viral approaches to gene therapy," Curr. Opin. Biotech., 4, 705–710; Ledley, F. D. (1994), "Non-viral gene therapy," Curr. Opin. Biotechnol., 5, 626–636).

Viral vector-directed gene transfer shows high gene transfer efficiency but is deficient in several areas. For example, some viral vectors randomly integrate DNA into host genomes (Olsen, J. C., Huang, W., Johnson, L. G., and Boucher, R. C. (1994) "Persistence of adenoviral vector gene expression in CF airway cells is due to integration of vector sequences into chromosomal DNA," Pediatr. Pulm. S10, 230; Russel, D. W., Miller, A. D., and Alexander, I. E. (1994) "Adeno-associated virus vectors preferentially transduce cells in S phase," Proc. Natl. Acad. Sci. 91, 8915–8919) posing potential risks, including neoplastic transformation (Colledge et al. (1994) supra; Fairbairn, L. J., Cross, M. A. and Arrand, J. R. (1994) "Paterson Symposium 1993-Gene therapy," Brit. J. Cancer, 59, 972–975). In addition, adenoviral vectors induce host inflammatory and immune responses, rendering these vectors ineffective in repeated application (Ginsburg, H. S., Moldawer, L. L., Schgal, P. B., Redimgton, M., Kilian, D. L., Chanock, R. M., and Prince, G. A. (1991), "A mouse model for investigating the molecular pathogenesis of adenovirus pneumonia," Proc. Natl. Acad. Sci. USA 88, 1651–1655; Yang, Y. P., Nunes, F. A., Berencsi, K., Gonczol, E., Engelhardt, J. F., and Wilson, J. M. (1994), "Inactivation of E2a in recombinant adenovirus improves the prospect for gene therapy in cystic fibrosis," Nature Genetics 7, 362–369; Yei, S., Mittereder, N., Tany, K., O'Sullivan, C., and Trapnell, B. C. (1994) "Adenovirus-mediated gene transfer for cystic fibrosis: Quantitative evaluation of repeated in vivo vector administration to the lung," Gene Therapy 1, 192–200; Trapnell et al. (1994), supra). Retroviral vectors require dividing cells for stable integration (Miller, D. C., Adam, M. A., and Miller, A. D. (1990), "Gene transfer by retrovirus vectors occurs only in cells that are actively replicating at the time of infection," Mol. Cell Biol. 10, 4239–4242), making these vectors unsuitable for gene therapy of terminally differentiated cells. Similarly, for efficient transduction, adeno-associated virus prefers cells in the S phase to the cells in stationary culture (Russel et al. (1994) supra). Furthermore, the requirement of adenovirus and high multiplicity of infection of adeno-associated virus for efficient transduction (Russel et al., (1994) supra) coupled with difficulty in obtaining virus preparations with high titer has limited the use of this virus as a routine gene therapy vector.

Some of the problems associated with using these viral vectors can be circumvented using gene transfer agents, such as molecular conjugates (Wu, G. Y. and Wu, C. H. (1987) "Receptor-mediated in vitro gene transformation by a soluble DNA carrier system," J. Biol. Chem. 262, 4429–4432; Wagner, E., Zenke, M., Cotten, M., Beug, H., and Birnstiel, M. L., (1990) "Transferrin-polycation conjugates as carriers for DNA uptake into cells," Proc. Natl. Acad. Sci., USA 87, 3410–3414; Findeis, M. A., Merwin, J. J., Spitalny, G. L., and Chiou, H. C. (1993), "Targeted delivery of DNA for gene therapy via receptors," TIBTECH 11, 202–205; Ferkol, T., Kaetzel, C. S., and Davis, P. B. (1993), "Gene transfer into respiratory epithelial cells by targeting the polymeric immunoglobulin receptor," J. Clin. Invest. 92, 2394–2400; Monsigny, M., Roche, A.-C., Midous, P., and Mayer, R. (1994) "Glycoconjugates as carriers for specific delivery of therapeutic drugs and genes," Adv. Drug Del. Rev. 4, 1–24; Yin, W. and Cheng, P-W. (1994), "Lectin conjugate-directed gene transfer to airway epithelial cells," Biochem. Biophys. Res. Commun., 205, 826–833) and cationic liposomes (Felgner, J. H., Gadek, T. R., Holm, M., Roman, R., Chan, H. W., Wenz, M., Northro, J. P., Ringold, G. M., and Danielsen, M. (1987) "Lipofectin: A highly efficient, lipid-mediated DNA-transfection procedure," Proc. Natl. Acad. Sci., USA 84: 7413–7417). Molecular conjugates are prepared by chemically linking receptor ligands with polycations (Wagner, E., Curiel, D., and Cotten, M. (1994), "Delivery of drugs, proteins and genes into cells using transferrin as a ligand for receptor-mediated endocytosis," Adv. Drug Del., Rev. 14, 113–135). Molecular conjugates for receptor-mediated gene delivery can also be prepared by chemically linking antibodies or fragments thereof with polycations (Cotten, M. and Wagner, E. (1993) supra; references therein and Ferkol, T. et al. (1993) supra). The polycations serve as carriers of DNA while the ligands target the receptors on cell surfaces. Upon binding to the receptors, the conjugates along with the DNA are internalized via receptor-mediated endocytosis (Findeis (1993) supra; Wagner (1994) supra; Curiel, D. T. (1994), "High-efficiency gene transfer employing adenovirus-polylysine-DNA complex," Nat. Immun., 13, 141–164).

In cationic liposome-mediated gene transfer, liposomes bind to DNA via ionic interaction and liposomes facilitate the delivery of DNA presumably by fusion with the plasma membrane (Felgner et al. (1987) supra) and/or endocytosis (Zhou, X. and Huang, L., (1994) "DNA transfection mediated by cationic liposomes containing lipopolylysine: characterization and mechanism of action," Biochem. Biophys. Acta., 1189, 195–203. These agents are easy to prepare, can deliver DNA of any size (Wagner et al. (1994) supra), but generally suffer from low transfection efficiency (Colledge (1994) supra).

SUMMARY OF THE INVENTION

This invention employs a delivery system for biologically active molecules which must enter cells to exert their biological effect. Such molecules include but are not limited to peptides, proteins, or polynucleotides such as DNA or RNA. In a preferred embodiment the molecule is a gene for transfection in gene therapy protocal. The delivery system is a mixture composed of a cationic lipid which is preferably in a liposome formulation and a receptor ligand, such as transferrin, wherein the ligand is not covalently bound to a liposome component. The receptor ligand is first added to the cationic liposome formulation and incubated. The biologically active agent to be delivered to cells is then added to the resulting ligand-liposome combination and the mixture is again incubated. The order in which the components are combined, i.e. ligand with liposome formulation followed by nucleic acid, is critical to obtaining high efficiency transfection.

Generally, the methods of this invention can employ any ligand having an affinity for a cell surface receptor. The term ligand is used broadly herein and includes receptor ligands such as transferrin, insulin, cholera toxin, adenovirus fiber KNOB peptide, as well as antibodies and antibody fragments (e.g. Fab fragments) to receptors, such as antisecretory components, and peptides and proteins, such as epidermal growth factor and viral proteins, particularly those viral proteins which the receptor-mediated endocytosis mechanism stimulates. The ligand employed can be one, such as transferrin or insulin, that targets a wide range of cell types or one that targets a specific cell type.

Generally, the methods of this invention can employ any mono-or polycationic lipid and neutral lipid in a cationic liposome formulation. Cationic lipids including DOTMA, DDAB, DOSPA, DORI, DORI-ester, DORI-ether, DMRIE, DOTAP, TM-TPS and cationic lipids structurally related thereto. [Definitions for each of these acronyms are provided herein and are well-known in the art.]

More specifically, this invention provides transfection agents in which the ligand is transferrin, insulin, cholera toxin or adenovirus fiber KNOB peptide, and in which the cationic liposome formulation comprises the cationic lipids DOTMA (N-[1-(2,3-dioleyloxy)propyl]-N,N,N-trimethyl), or DDAB (dimethyl dioctadecylammonimum bromide) and an appropriate neutral lipid. Useful cationic liposome formulations include those in which the neutral lipid is DOPE (dioleoyl phosphatidylethanolamine). Preferred cationic liposome formulations are "lipofectin" (Trademark) which is a commercially available 1:1 liposome formulation of DOTMA and DOPE and "lipofectace" (Trademark) which is a commercially available 1:2.5 liposome formulation of DDAB and DOPE.

Certain fractions and/or components of serum have been found to enhance transfection efficiency of cationic liposomes. These fractions or components, when used in place of receptor ligands in the protocols of this invention, enhance liposome transfection efficiency.

The method of this invention is a high-efficiency gene transfer method which employs transfection reagents that are easy to prepare. In exemplified embodiments the reagent ingredients are commercially available. Further, receptor ligands prepared from one animal source may be employed for gene therapy in the same animal species, thus mitigating or preventing host inflammatory and immune responses which have been a major drawback for human gene therapy employing adenoviral vectors. Liposomes appear to cause little or no apparent host inflammatory and immune response. Utilization of human transferrin or other human ligands in combination with cationic liposomes can circumvent the host immune response while achieving high gene transfer efficiency in humans.

The methods described herein with "lipofectin" and transferrin can yield 100% transfection efficiency in HeLa cells. The "lipofectin"-transferrin transfection protocol of this invention can also be used to correct the chloride conductance abnormality in immortalized CF airway epithelial cells (CFT1) by delivery of CFTR CDNA. Transferrin also significantly enhances transfection by "lipofectace" of HeLa cells.

The transfection agents and methods of this invention are useful in in vitro and in vivo transfection applications. The simplicity of the formulation and high transfection efficiency by these reagents facilitate the development of suitable transfection reagents for human gene therapy.

BRIEF DESCRIPTION OF THE FIGURES

FIG. 7 is a graph similar to that of FIG. 6 plotting percent $^{36}$Cl$^-$ remaining as a function of time in transfected cells. Open circles (○) indicate the control (CFT1 cells transfected with "lipofectin"); closed circles (●), open squares (□) and closed diamonds (♦) indicate the results for cells transfected with cholera toxin, insulin or transferrin, respectively in combination with "lipofectin" and pCMVCFTR. Cells were preloaded with Na$^{36}$Cl in Cl$^-$ containing medium. Media were collected and replenished with fresh Cl$^-$ -free medium with 0.1 mm ameloride at 1 min intervals. At the end of 3 min, 10 μμ forskolin was added to the media.

DETAILED DESCRIPTION OF THE INVENTION

Figure 1A:
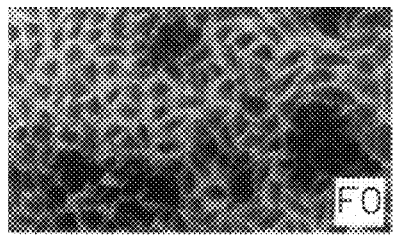
FIGS. 1(a)–(h) illustrates X-Gal staining of HeLa cells transfected with transferrin and "lipofectin" containing either 16 or 0 μg transferrin (F0) (1a), and the transfected cells of six consecutive passages (F1 to F6)(1b–1g). Cells transfected with "lipofectin"-DNA, i.e. 0 μg transferrin, served as the controls (C)(1h). For each set of F0, cells in 9 wells were transfected. After culturing for 48 hours following transfection, cells in 3 wells were stained with X-gal, cells in another 3 wells were assayed for β-galactosidase activity, and cells in the remaining 3 wells were subcultured to 9 wells and employed for subsequent study. The subcultured cells were processed as described below but without transfection. Only F0(C) (1h) is shown because F1(C) and F2(C) are similar to F5(1f), and F3(C), F4(C), F5(C), and F6(C) are similar to F6(1g). A detailed experimental protocol is described in the Examples.
Figure 1E:
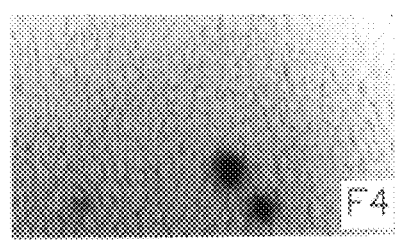
Figure 1B:
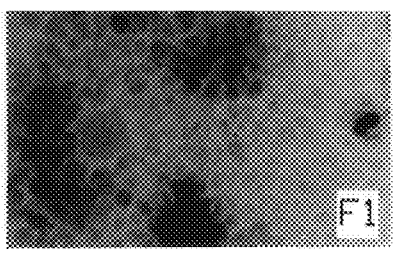
Figure 1F:
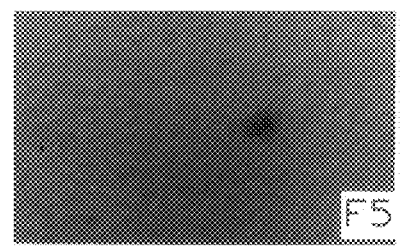
Figure 1C:
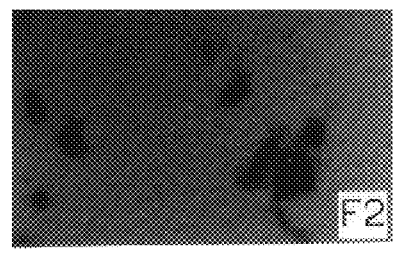
Figure 1G:
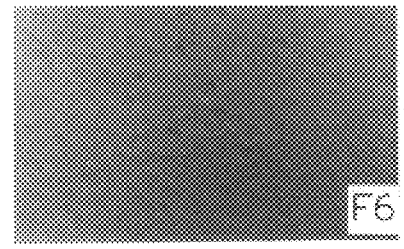
Figure 1D:
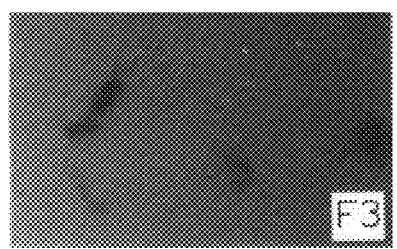
Figure 1H:
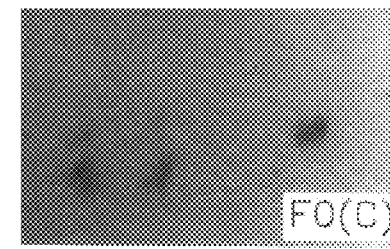

The present invention is in part based on the observation of 98–100% transfection of HeLa cells employing the cationic liposome formulation "lipofectin" and the wide cell range receptor ligand transferrin to deliver an expressible β-galactosidase gene. By comparison simple lipofection using "lipofectin" alone gave low transfection efficiency (3–4%) of the same DNA construct into HeLa cells. The β-galactosidase DNA construct alone or in combination with transferrin gave even lower transfection efficiencies with HeLa cells (<0.01%), even though the DNA could form a complex with transferrin.

The order of combining the components of the transfection composition was critical to transfection efficiency. The cationic liposome formulation is prepared by conventional methods. The receptor ligand is added to the liposome formulation and the mixture is incubated at room temperature to allow equilibration of complex formation. The nucleic acid, e.g., DNA construct, to be delivered is then added and the mixture incubated a second time at room temperature to allow equilibration of complex formation. Addition of the nucleic acid to the cationic liposome formulation followed by addition of transferrin does not give a high efficiency transfection agent. Likewise, simultaneous combination of nucleic acid, liposome formulation and receptor ligand does not give a high efficiency transfection agent.

Transferrin receptor-mediated endocytosis is a normal physiological process by which transferrin delivers iron to the cells (Hueber, H. A. and Finch, C. A., (1987) "The physiology of transferrin and transferrin receptors," Physiol. Rev. 67, 520–582). The process entails initial binding of holotransferrin to its receptor on the cell surface at neutral pH (Aisen, P. (1994), "The transferrin receptor and the release of iron from transferrin," Adv. Exp. Med. Biol., 356, 31–40). The transferrin-receptor complex is then internalized to form a clathrin-coated vesicle. Following the release of bound iron as acidic pH in the endosome, the transferrin, still complexed to the receptors, escapes from the endosome and returns to the cell surface where it is released into the circulation. This efficient receptor recycling process has been exploited to deliver foreign DNA to the cells by employing transferrin-polycation conjugates (Wagner et al., 1987; Cotten and Wagner (1993) supra; Wagner et al. (1994) supra; Yin and Cheng, (1994) supra). However, these molecular conjugates have low transfection efficiency (Colledge, (1994) supra; Yin and Cheng, (1994) supra).

The reason for the dramatic enhancement of transfection efficiency observed when transferrin is included in the cationic liposome transfection reagent, but not covalently bound to a liposome component, is not entirely clear at the present time. The role of the cationic liposome in transfection has been thought to be to bind to the negatively charged groups on the cell surface and to fuse with the plasma membrane. During this process, the DNA (and any other species) carried by the cationic liposome gained entrance to the cells (Felgner et al. (1987) supra). An alternative proposal is that the cationic liposome brought the DNA to the cells via the endocytosis pathway (Zhou and Huang (1994) supra).

Figure 4:
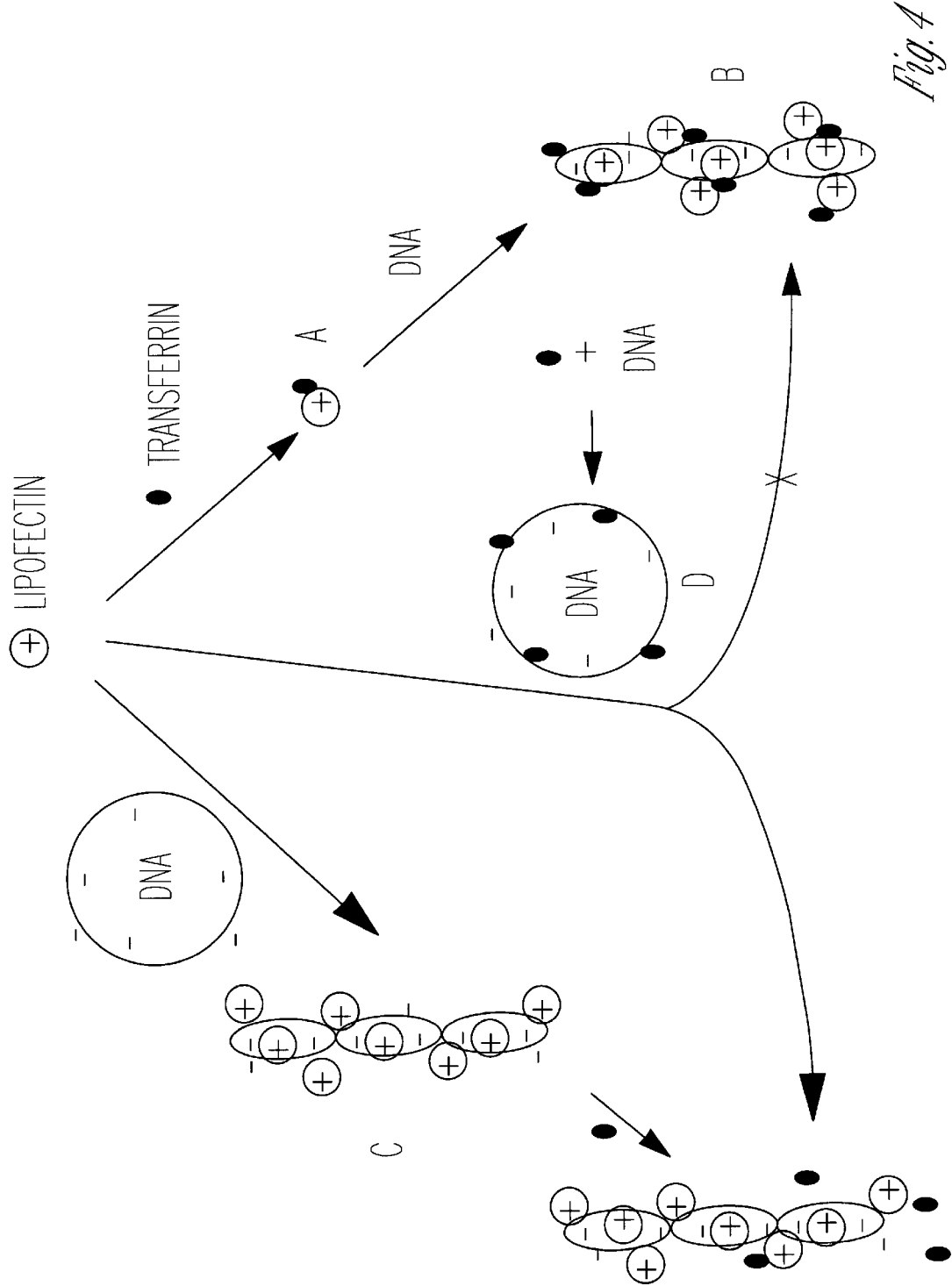
FIG. 4 illustrates the proposed scheme for the formation of efficient and inefficient gene transfer complexes employing the gene transfer vector composed of transferrin and "lipofectin". These complexes are designated as: (A) "lipofectin"-transferrin, (B) "lipofectin"-DNA-transferrin, (C) "lipofectin"-DNA, and (D) transferrin-DNA. (C) and (D) are inefficient gene transfer complexes while (B) is the most efficient gene transfer complex. The relative strength of interaction between each pair of components are: "lipofectin"-DNA>>transferrin-DNA>>transferrin-"lipofectin".

In the gene transfer method of this invention, transferrin in combination with liposomes facilitates the entry of DNA into the cells at a level twice that of liposomes without transferrin. Although not wishing to be bound by any particular theory of action, high-efficiency gene transfer is believed to be mediated by "lipofectin"-DNA-transferrin complex B as depicted in FIG. 4. The proposed scheme for the formation of effective and ineffective gene transfer complexes illustrated in FIG. 4 is based on the following observations:

1) "Lipofectin" readily forms a complex with a polynucleotide such as DNA through charge-charge interactions and this type of interaction is strong enough to survive electrophoresis conditions. Gershon, H. Ghirlando, R. Guttman, S. B. and Minsky, A. (1993) "Mode of formation and structural features of DNA-cationic liposome complexes used for transfection" Biochemistry 32:7143–7151 reported that interaction of "lipofectin" with DNA led to the formation of condensed structures as a result of interrelated lipid fusion and DNA collapse, as depicted in complex C of FIG. 4. The exposed surface of the condensed structure is considerably smaller than that of the extended DNA molecule.

Figure 3:
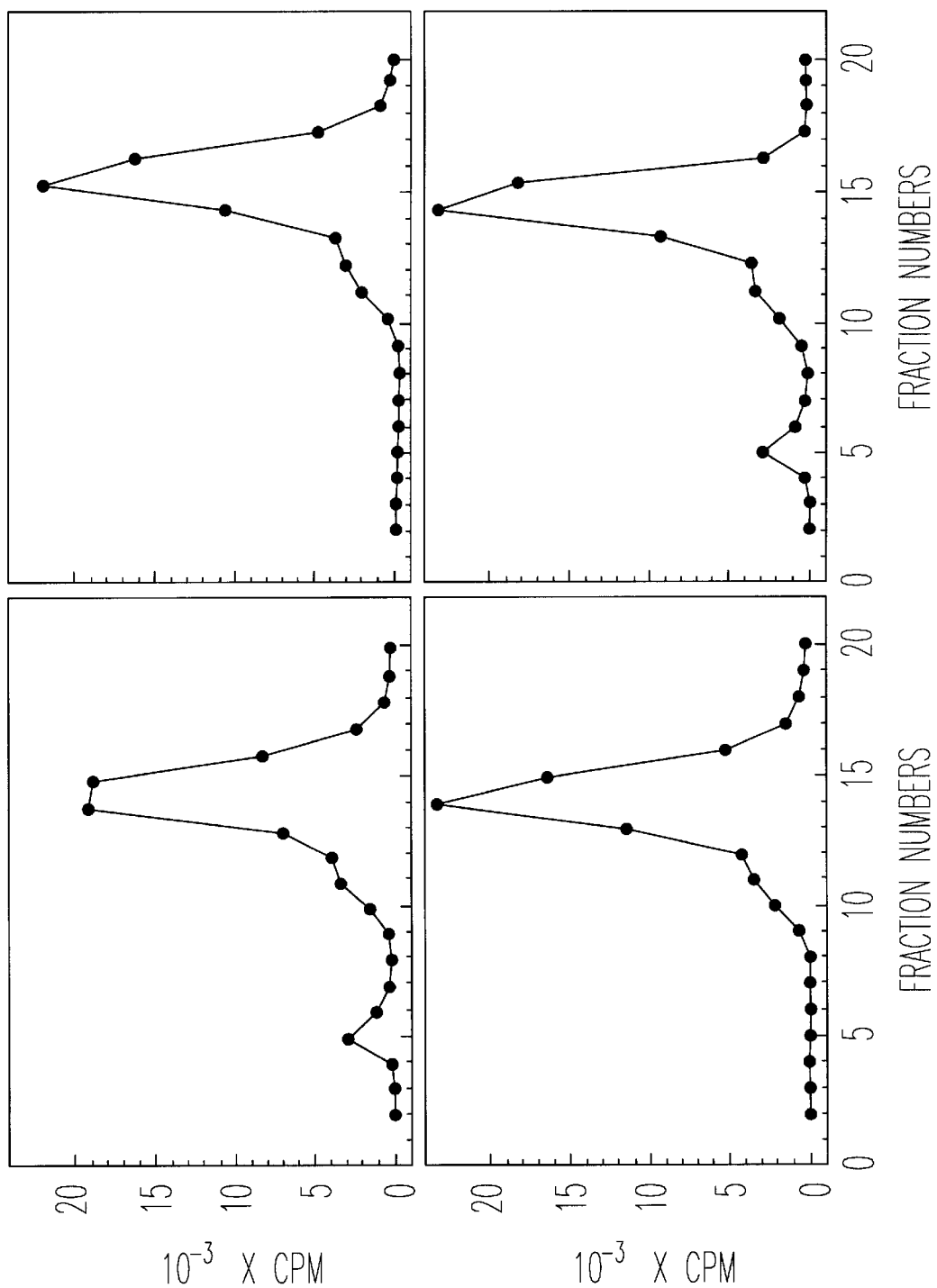
FIG. 3 illustrates Sepharose 4B chromatography of the mixture of (A) [$^{125}$I]transferrin, "lipofectin", and DNA, (B) "lipofectin", DNA, and [$^{125}$I]transferrin, (C) "lipofectin" and [$^{125}$I]transferrin, and (D) DNA and [$^{125}$I]transferrin. Each component of the mixtures was added sequentially followed by a 15 min incubation period. The % of radioactivity detected in the void volume is indicated.

2) DNA can form a complex with transferrin, as demonstrated by Sepharose 4B chromatography (See, FIG. 3D). Because transferrin is an ampholyte with an isoelectric point of 5.9, the small numbers of positively charged groups present in transferrin at pH 7.4 may be responsible for this interaction. Failure of transferrin to retard the mobility of DNA in agarose gel electrophoresis also supports the notion that the binding between DNA and transferrin is not very strong.

3) "Lipofectin" binds transferrin weakly (FIG. 3C) presumably through the negatively charged groups in transferrin at physiological pH. This interaction may not be strong enough to allow the "lipofectin"-transferrin complex to survive the conditions employed for sepharose 4B chromatography. However, it may be strong enough to permit transferrin to partially shield the positively charged groups of the "lipofectin" from binding to the DNA and at the same time enable the DNA to bind to "lipofectin" and transferrin. As a result, an efficient gene transfer complex is formed (FIG. 4, complex B).

4) The transfection reagents prepared by exposing "lipofectin" to DNA followed by a) transferrin, b) DNA and transferrin added simultaneously, or c) pre-formed DNA-transferrin complex, all have low transfection efficiency. These observations may be the result of the formation of ineffective gene transfer complexes as depicted in FIG. 4 (complex C). When all three components are present, "lipofectin"-DNA complex will be formed prior to the formation of other complexes, which leads to the formation of the inefficient gene transfer complexes.

In addition to its role in facilitating the entry of DNA to the cells, transferrin may play important roles in other steps of the gene expression process. For example, following the internalization of the "lipofectin"-DNA-transferrin-transferrin receptor complex, transferrin may facilitate the escape of DNA from the endosome. Because escaping from the endosome is a normal physiological process for transferrin and its receptor complex (Hueber (1987) supra; Aisen, (1994) supra) the entrapped DNA in the endosome may escape by following the transferrin and its receptor complex presumably via a bystander effect. Whether the enhancement of the transfection efficiency by transferrin is the result of this bystander effect or through other mechanisms remains to be elucidated. This mechanism may function as well with other cell receptor ligands, such as insulin.

It is believed that the scheme illustrated in FIG. 4 for "lipofectin" and transferrin is general and applicable to any receptor ligand including insulin, cholera toxin and the KNOB peptide and any mono- or polycationic liposome formulation and in particular also applies to "lipofectace" formulations and DC-cholesterol cationic liposomes with transferrin.

The high-efficiency gene transfer method of this invention particularly when monocationic lipids "lipofectin" or "lipofectace" are employed in combination with receptor ligands offers several advantages. The transfection reagent is easy to prepare, in several cases all of the ingredients are commercially available. Ligands prepared from one animal source may be employed for gene therapy in the same animal species, thus preventing host immune response to the vector. The host inflammatory and immune responses have been a major drawback for human gene therapy employing adenoviral vectors. (Ginsburg et al. (1991) supra; Trapnell et al. (1994) supra; Yang et al. (1994) supra; Yei et al. (1994) supra). Recent liposome toxicity studies in the lungs of humans show that liposome appears to cause minimal or no host inflammatory and immune response. (Thomas, D. A., Myers, M. A., Wichert, B., Schreier, H., and Gonzalez, R. J. (1991), "Acute effects of liposome aerosol inhalation on pulmonary function in healthy human volunteers," Chest. 99, 1268–1270) and several animal species (Stribling, R., Brunette, E., Liggitt, D., Gaensler, K., and Debs, R. (1992), "Aerosol gene delivery in vivo," Proc. Natl. Acad. Sci., USA 89, 11277–11281; Alton, E. W. F. W., Middleton, O. G., Caplen, N. J., Smith, S. N., Steel, D. M., Munkonge, F. M., Jeffery, P. K., Geddes, D. M., Hart, S. L., Williamson, R., Fasold, K. I., Miller, A. D., Dickinson, P., Stevenson, B. J., McLachlan, G., Dorin, J. R., and Porteous, D. J. (1993), "Non-invasive liposome-mediated gene delivery can correct the ion transport defect in cystic fibrosis mutant mice," Nature Genetics, 5, 135–142; Canonico, A. E., Plitman, J. D., Conary, J. T., Meyrick, B. O., and Brigham, K. L. (1994), "No lung toxicity after repeated aerosol or intravenous delivery of plasmid-cationic liposome complexes," J. Appl. Physiol., 77, 415–419; San, H., Yang, Z.-Y., Pompili, V. J., Jaffe, M. L., Plautz, G. E., Xu, L., Felgner, J. H., Wheeler, C. J., Felgner, P. L., Gao, X., Huang, L., Gordon, D., Nabel, G. J., and Nabel, E. G. (1993), "Safety and short-term toxicity of a novel cationic lipid formulation for human gene therapy," Hum. Gene Ther. 4, 781–788.) Utilization of human transferrin or other human ligands in combination with cationic liposomes may circumvent the host immune response while achieving high gene transfer efficiency in humans.

Transfection efficiency enhancement exhibited with transferrin differs among different cationic liposomes. As shown in Table 4, transferrin significantly enhances (10-fold or more enhancement of % blue cells or β-Gal activity) transfection with "lipofectin" and "lipofectace" liposome formulations. Enhancement is also observed with DC-cholesterol liposomes, but no measurable enhancement is observed "lipofectamine", which contains the polycationic lipid DOSPA.

U.S. Pat. No. 4,897,355 (Eppstein et al.) issued in 1990 discloses cationic lipids related in structure to DOTMA. The cationic lipids and representative neutral lipids disclosed therein are useful in the cationic liposome formulations of this invention.

DDAB is the monocationic lipid dimethyl dioctadecylammonium bromide. See U.S. Pat. No. 5,279,833 and WO 91/15501 (published Oct. 17, 1991 for DDAB and related cationic lipids). Related cationic species, for example, those in which the octadecyl groups are replaced with other higher alkyl groups (those alkyl groups having 8 or more carbon atoms); those in which the methyl groups are replaced with other lower alkyl groups (those alkyl groups having 1 to about 3 carbon atoms); or those in which the bromide anion is replaced with another anion are useful in the cationic liposome formulations of this invention.

Singhal, A. and Huang, L. (1994) "Direct Gene Transfer by Liposomes" J. Liposome Res. 4(1):289–299) describe cationic derivatives of cholesterol useful in preparation of cationic liposomes. Cholesterol derivatives in which a tertiary amino group is linked to a lipid anchor with an amide or carbamoyl bond and separated by a spacer of 3–6 atoms can be used to prepare liposomes with high transfection efficiency, increased shelf life and low toxicity. See also: Gao, X. and Huang, L. (1991) "A novel cationic liposome reagent for efficient transfection of mammalian cells" Biochem. Biophys. Res. Commun. 179:280–285; Farhood, H. Bottega, R. Epand, R. M. and Huang, L. (1992) "Effect of cationic cholesterol derivatives on gene transfer and protein kinase C activity" Biochem. Biophys. Acta 1111:239–246. DC-cholesterol is the derivitized cholesterol: 39-[N-(N',N'-dimethylaminoethane)-carbamoyl]cholesterol. DC-cholesterol liposomes are prepared by combining the cationic lipid with a neutral lipid, for example DOPE.

"Lipofectamine" is a 3:1 liposome formulation of the polycationic lipid 2,3-dioleyloxy-N-[2(sperminecarboxamido)ethyl]-N,N-dimethyl-1-propanaminiumtrifluoroacetate (DOSPA) and DOPE. See U.S. Pat. No. 5,334,761.

"Cellfecin" (Trademark) is a commercially available cationic liposome formulation which is a 1:1.5 (w/w) formulation of the polycationic lipid N,N',N",N"'-tetrapalmitylspermine (TM-TPS) and DOPE. TM-TPS and related polycationic lipids useful in this invention are described in WO95/17373 (published Jun. 29, 1995).

U.S. patent application Ser. No. 08/195,866 filed Feb. 11, 1994 (Gebeyehu et al.) discloses other cationic lipids that are useful in the method of the present invention. Of particular interest are urethane derivatives disclosed therein.

U.S. Pat. No. 5,264,618 describes cationic lipids such as DOTAP (1,2-bis(oleoyloxy)-3-(trimethylammonio)propane. These lipids differ from DOTMA in that the oleoyl moieties are linked via ester rather than ether bonds to the propyl amine. A group of cationic lipids related in structure to DOTMA and DOTAP are those in which one of the methyl groups of the trimethylammonium group is replaced with a hydroxyethyl group. Compounds of this type are similar to the Rosenthal Inhibitor (RI) of phospholipase A (Rosenthal, A. F. and Geyer, R. P. (1960) J. Biol. Chem. 235:2202–2206) which has stearoyl esters linked to the propylamine core. The dioleoyl analogs of RI are commonly called DORI-ether or DORI-ester, depending on the linkage of the fatty acid moieties to the propylamine core. The hydroxyethyl group of such analogs can also be further functionalized for example by esterification. All of these cationic lipids structurally related DOTMA are useful in the cationic liposome formulations of this invention. Another cationic lipid useful in liposome formulations of this invention is 1,2-dimyristyloxypropanol-3,3-dimethylhydroxymethylammoniumbromide, which is often referred to as the acronym DMRIE.

As noted herein, this gene transfer method is generally applicable to any receptor ligand. Cotten and Wagner (1993) supra in a review of non-viral approaches to gene therapy provide, in Table 1 therein, a non-exhaustive list of species useful as receptor ligands for conjugate formation in receptor-mediated gene delivery. The specifics of the individual ligands is described in references cited therein. Other examples of receptor ligands for cell targeting are found in other references cited herein. Enhanced transfection of this invention has been demonstrated using transferrin, insulin and cholera toxin as receptor ligands. All of the ligands described in the Cotten and Wagner (1993) reference and other references cited herein can also function for enhanced transfection without covalent binding of the ligand as described in this invention. Therefore, this gene transfer protocol is applicable generally to ligands which can be internalized upon binding to cell surface receptors.

The specific examples provided herein show transient expression of DNA delivered to cells by receptor-facilitated liposome transfection. Failure to detect a population of the transfected cells which expressed β-galactosidase suggests that despite the high-efficiency gene transfer obtained by using this transfection agent, integration of the plasmid DNA into the host genome is still a rare event. The receptor ligand facilitated gene transfer protocol of this invention can be employed with any known techniques for achieving integration of nucleic acid, e.g., DNA, into the host genomic DNA.

The method of this invention can be employed with any known techniques for enhancing expression of nucleic acid, e.g., DNA, introduced into the cell. For example, cointroduction of nuclear protein along with DNA in liposomes can result in enhanced express of the DNA. Kaneda, Y. Iwai, K. and Uchida, T. (1989) "Increased Expression of DNA Cointroduced with Nuclear Protein in Adult Rat Liver" Science 243:375–378; Kaneda, Y. Iwai, K. and Uchida, T. (1989) "Introduction and Expression of the Human Insulin Gene in Adult Rat Liver" J. Biol. Chem. 264(21):12126–12129 Nuclear protein, such as non-histone chromosomal protein, high mobility group 1 (HMG-1), is believed to facilitate delivery of DNA to cell nuclei thus enhancing expression. The method of this invention can be employed to cointroduce DNA and nuclear protein to achieve further enhancement of expression.

Those of ordinary skill in the art will appreciate that certain details of the preparation of transfection agents of this invention and details of transfection protocols can be routinely varied to achieve optimal transfection efficiency and gene expression for a given receptor ligand, cationic lipid/neutral lipid liposome formulation, nucleic acid and target cell type. Such routine optimization is within the spirit and scope of their invention.

Those of ordinary skill in the art will also appreciate that all receptor ligands, cationic lipids, and neutral lipids other than those specifically exemplified herein can be employed in view of the descriptions herein in the compositions and methods of this invention.

The transferrin-cationic liposome protocol of this invention has been described for use in introduction of nucleic acids into cells. The transferrin-cationic liposome protocol of this invention can be readily adapted by reference to this disclosure and techniques and methods well known in the art to introduction of drugs and proteins as well as genes into cells. Wagner et al. (1994) supra is a review of delivery of a variety of species using receptor-mediated endocytosis.

All references including journal articles, patents, and patent applications cited in this specification are incorporated in their entirety by reference herein. References cited provide inter also details of the structures of various cationic lipids and neutral lipids useful in preparation of cationic liposomes, methods of preparing liposomes and liposome formulations, sources of cell surface receptor ligands including methods for isolating or otherwise preparing such ligands, descriptions of cell growth conditions, details of the use of receptor ligands for targeted transfection and descriptions of in vitro and in vivo applications of transfection agents and methods.

The following examples illustrate the invention and are in no way intended to limit the scope of the invention.

THE EXAMPLES

Example 1

Transfection of HeLa Cells with "Lipofectin" and Transferrin

Methods:

Determination of Optimal Ratios of "Lipofectin" and DNA

Initial agarose gel electrophoresis was performed on mixtures of varying amounts (0.5–10 μg) of "lipofectin" (Trademark) (GIBCO/BRL, Gaithersburg, Md.) at fixed amounts (1.5 μg) of DNA (pCMVlacZ) (Clontech Lab, Inc., Palo Alto, Calif.) to determine the optimal ratio of "lipofectin" and DNA. The DNA in agarose gel was stained with ethidium bromide and visualized under a UV light. When complexed with "lipofectin", the DNA would not enter the gel. The same agarose gel electrophoresis procedure was employed to assess whether transferrin could retard DNA mobility by analyzing mixtures of 1.5 μg DNA and 2–32 μg transferrin.

Sepharose 4B Chromatography:

To assess whether transferrin was complexed with "lipofectin"-DNA complex, a transfection solution (500 μL) which contained 32 μg of [$^{125}$I] transferrin (7×10$^4$ μm) in 100 μL HEPES-buffered saline (HBS) (20 mM HEPES, pH 7.4 and 100 mM NaCl), 3 µg of "lipofectin", 1.5 µg of pCMVlacZ, and 300 µL of DMEM- H (GIBCO/BRL) was applied to a Sepharose 4B column (1×12 cm). The order of addition of transferrin, "lipofectin", and DNA varies according to the specific experimental protocol. The mixture was gently mixed and then incubated for 15 min after the addition of each reagent. Then, the column was developed with HBS, fractions of 0.5 mL collected, and radioactivity measured in a c-counter. "Lipofectin" was eluted at the void volume (3 mL) and unbound [$^{125}$I] transferrin at 8.4–9.0 mL elution volume. DNA-"lipofectin"-transferrin and DNA-transferrin complexes appeared at the void volume.

Gene Transfer Protocol:

HeLa cells (American Type Culture, Rockville, Md.) which had been grown to confluence in a 48-well culture plate in DMEM-H medium containing 10% fetal bovine serum (FBS) were rinsed two times with serum-free DMEM-H. These cells were then exposed to 500 µL of transfection solution prepared as described below. In 12×75 mm polystyrene tubes (Becton Dickinson, Lincoln Park, N.J.), the following reagents were sequentially added, gently mixed, and incubated for 15 min at room temperature after each addition: 100 µL of HBS containing predetermined amounts of freshly prepared human transferrin (iron-saturated, heat inactivated, (Collaborative Biomedical Products, Becton Dickinson, Bedford, Mass.) (32 µg for routine experiments), 3 µL of "lipofectin" (1 mg/mL), and 100 µL of HBS containing 1.5 µg of pCMVlacZ. The mixture was transferred to each well which had been covered with 300 µL of serum-free DMEM-H without antibiotics and then gently mixed. The plate was incubated for predetermined amounts of time (18–24 h for routine experiments) under water saturated environment and 5% $CO_2$. The corresponding cultures exposed to "lipofectin"-DNA served as a control. The other two controls included DNA and DNA plus transferrin. The conditioned media were then replaced with 1.0 mL of DMEM-H containing 10% FBS and antibiotics (50 U/mL penicillin and 50 µg/mL streptomycin). After culturing for 48 h, cells in three wells were fixed in 300 µL of ice cold 2% paraformaldehyde— 0.20% glutaraldehyde for 10 min following removal of the conditioned medium and washing twice with PBS. The cells were then exposed to 0.5 mL of 1.0 mg/mL 5-bromo-4-chloro-3-indolyl-β-D-galactopyranoside (X-Gal) (GIBCO/BRL) (Yin and Cheng (1994) "Lectin conjugated-directed gene transfer to airway epithelial cells," Biochem. Biophys. Res. Commun. 205:826–833), at 37° C. for two days after the fixatives had been removed and rinsed twice with PBS. The percentage of blue cells was measured by counting the number of blue cells out of a total of 2,500–3,000 cells in 20–30 randomly chosen fields under a phase-contrast microscope. Cells in three other wells were rinsed three times with PBS, dissociated by trypsinization, rinsed three times with PBS, and then lysed by three cycles of freezing and thawing. These lysates were measured for β-galactosidase activity as light units (Beale et al. (1992) "A rapid and simple chemiluminescent assay for Escherichia coli β-galactosidase," Biotechniques 120:320–324) on a Lummat LB9501 spectrofluorimeter (EG&G Berthold, Nashua, N.H.) and measured for protein (Bradford Reagent, Bio-Rad, Melville, N.Y.) using bovine serum albumin (BSA) as the standard. The data were expressed as light units per µg protein.

Transfer of $^{35}$S-pCMVlacZ to HeLa Cells:

$^{35}$S-labelled pCMVlacZ was prepared by random priming (Boehringer-Mannheim, Indianapolis, Ind.) after linearization by EcoRI digestion. Each of the four transfection solutions, DNA, DNA+transferrin (32 µg), DNA+ "lipofectin" (3 µg), and DNA+"lipofectin"+transferrin, contained 1.5 µg of $^{35}$S-labelled pCMVlacZ (1.4×10$^4$ cpm). At 0, 0.5, 1, 3, 6, and 24 h after transfection, media were removed. Then, the cells were washed once with 1 mL HES, recovered by trypsinization, and washed twice with 1.5 mL HES. The pelleted cells were suspended in 60 µL of distilled water and ruptured by freezing and thawing three times. Aliquots were measured for radioactivity and protein. The data were expressed as cpm/mg protein.

Other Methods:

pCMVlacZ was purified from Escherichia coli, which harbors this plasmid DNA. using a QiaGen plasmid isolation kit (Chatsworth, Calif.). [$^{125}$I] Transferrin was prepared by a chloramine-T method as described below. 5 µL of 100 mCi/mL Na$^{125}$I (Amersham, Arlington Hts., Ill.) and 5 µL of 2 mg/mL chloramine T (Eastman Kodak Company, Rochester, N.Y.) were added to 100 µL HBS containing 100 µg transferrin. After incubation for 20–30 sec, 5 µL of sodium metabisulfite (Sigma, St. Louis, Mo.) was added to stop the reaction. The [$^{125}$I] transferrin was isolated on sephadex G-25 (0.5×4 cm).

Statistical Analysis:

Statistical analysis was performed by a two-tailed, unpaired t-test program (GaphPAD InPlot Software, San Diego, Calif.).

RESULTS

Gene Transfer Efficiency as a Function of Transfection Times:

Exposure of HeLa cells to the transfection solution composed of transferrin, "lipofectin," and pCMVlacZ for various periods of time from 0.5 to 24 hours resulted in increased expression of β-galactosidase as assessed by both β-galactosidase activity and percentage of blue cells (Table 1). A 2.5-fold increase of β-galactosidase activity in the cells transfected with the reagent prepared from transferrin, "lipofectin", and DNA over that of the control (p=0.0005) was observed after 0.5 h exposure even though the % blue cells did not differ between these two groups. Exposure for 1 h gave rise to 13-fold increase in β-galactosidase activity and 30% blue cells. After 5 h exposure, essentially all the cells were transfected. Similarly, β-galactosidase activity increased steadily for up to 5 hours and began to level off afterwards. For routine gene transfer experiments, overnight transfection was chosen in order to maximize the expression of β-galactosidase activity. In other controls which employed DNA or DNA plus transferrin, <0.01% of the cells were transfected.

Transfection Efficiency as a Function of Transferrin Amounts:

The transfection efficiency obtained with the mixture of transferrin, "lipofectin", and DNA was dependent on the amounts of transferrin employed. As shown in Table 2, the percentage of cells transfected and the β-galactosidase activities expressed in the transfected cells were increased when ≦µg of transferrin were used. In addition, when the amounts of transferrin used reached 8 µg and above, at least 97% of the HeLa cells were transfected. However, maximal expression of β-galactosidase activity was not obtained until 16 µg of transferrin was used.

Expression of Transfected Reporter Gene as a Function of Passage Numbers:

The high transfection efficiency in HeLa cells mediated by "lipofectin" plus transferrin afforded an excellent opportunity to examine the question for how many passages would the expression of the delivered reporter gene be maintained. As shown in FIG. 1 and Table 3, the percentage of transfected cells that were stained blue decreased progressively from 70% after one passage to <0.01% after 6 passages. Progressive decrease of β-galactosidase activity as a function of passage number was also observed.

Characterization of the Transfection Agent:

Agarose gel electrophoresis of the mixtures that contained fixed amount of DNA (1.5 μg) and varying amounts of "lipofectin" (0.5–10 μg) showed that all the DNA was complexed with "lipofectin" when "lipofectin" was at least two-to-three times the DNA amounts (w/w). This result formed the basis for the experimental protocol of employing 3 μg of "lipofectin" and 1.5 μg of DNA for each well of the 48-well plate.

Figure 2:
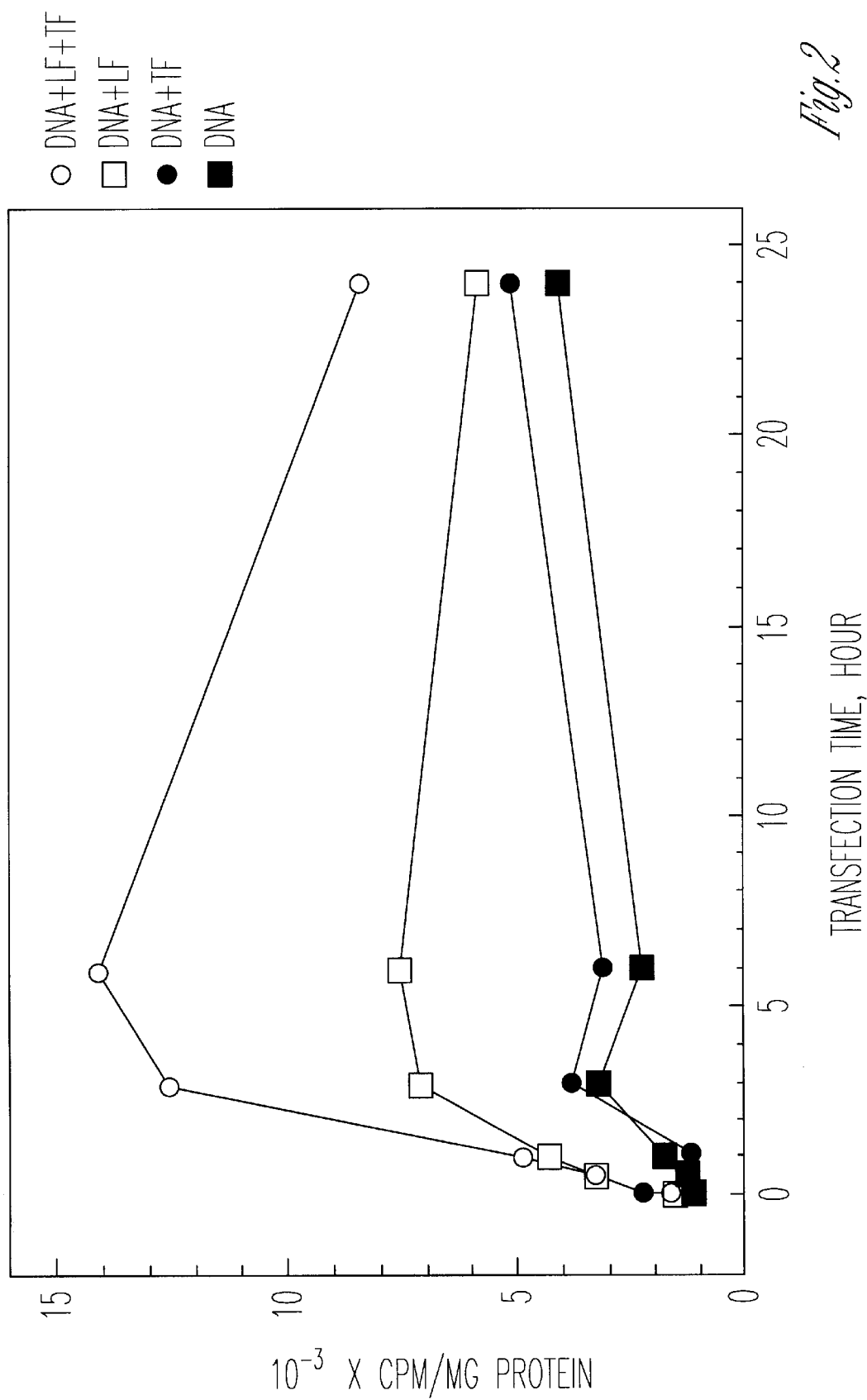
FIG. 2 illustrates enhancement of DNA transfer by transferrin in the presence of "lipofectin". The symbols ■, ●, □, and ○ represent $^{35}$S-pCMVlacZ transferred to the cells with DNA, DNA+transferrin, DNA+"lipofectin", and DNA+"lipofectin"+transferrin, respectively. The value at each time point was the average of two measurements.

To assess whether the observed increased expression of β-galactosidase was the result of increased transfer of DNA, a gene transfer experiment employing [$^{35}$S]DNA was performed. As shown in FIG. 2, in the absence of "lipofectin", transferrin did not increase DNA transfer over that with DNA alone. The maximal amount of DNA transferred by the "lipofectin"-DNA complex was at least two times that by DNA only. Incubation of transferrin with "lipofectin" prior to the addition of DNA doubled the amount of DNA delivered by "lipofectin"-DNA complex. By 24 h, the amount of DNA found in the cells transfected with the reagent prepared by sequential addition of transferrin, "lipofectin", and DNA decreased by 40%.

To assess the interactions among the different components in the transfection solution, Sepharose 4B column chromatography was performed. Analysis of the transfection solution prepared by sequential addition of 32 μg [$^{125}$I] transferrin, 3 μg "lipofectin", and 1.5 μg DNA showed that 6.8% of total radioactivity was eluted in the void volume (FIG. 3A). No radioactivity was detected in the void volume when the solution was prepared in the order of DNA, "lipofectin", followed by [$^{125}$I]transferrin (FIG. 3B). The transfection efficiency (3.2%) employing the reagent prepared the same way was not different from the control value (3.9%) obtained by transfection with "lipofectin" plus DNA. Only a small amount (0.2%) of radioactivity was detected in the void volume when the mixture of [$^{125}$I]transferrin and "lipofectin" was analyzed (FIG. 3C). In addition, when [$^{125}$I]transferrin was mixed with DNA, 6.8% of the radioactivity was also found in the void volume (FIG. 3D). The transfection efficiency (2.8%) employing transferrin plus DNA was the same as the control (data not shown). In addition, addition of 2–32 μg transferrin to 1.5 μg DNA did not decrease the mobility and the band intensity of the DNA on agarose gel electrophoresis.

Variation of Transferrin-facilitated pCMVlacZ Transfection Efficiency with Different Cationic Liposomes The transfection efficiency of transferrin-facilitated gene transfer in HeLa cells varied with different cationic liposomes. As shown in Table 4, "lipofectin" was the most effective liposome among the four different cationic liposomes examined. This was followed by "lipofectace" and then DC-cholesterol. "Lipofectamine" exhibited no enhancement in the results listed in Table 4. It may be, however, that the experiment with "lipofectamine", the results of which are listed in Table 4, does not accurately reflect the usefulness of "lipofectamine" as a cationic liposome component in methods of this invention. "Lipofectamine" only is generally found to be a reasonably efficient transfection agent into HeLa cells. Transfection efficiencies of 40% of DNA are routinely observed with "lipofectamine" alone. See Hawley-Nelson, P. et al. (1993) FOCUS 15:73. The percentage of blue cells observed in the experiment of Dable 4 for "lipofectamine" alone appears to be significantly lower than would normally be expected. This suggests some problems with the transfection experiment.

EXAMPLE 2

Correction of the Chloride Transport Abnormality of CFT1 Cells by Transferrin-facilitated Gene Transfer Mediated by Cationic Liposomes CFT1 cells grown to confluence in 48-well plates were exposed for 24 h to a transfection solution that contained "lipofectin", DNA, and transferrin.

The transfection solution was prepared as in Example 1. Specifically, transferrin was added to "lipofectin" and the mixture was incubated at room temperature for about 15 min. Thereafter, the DNA was added and the mixture was again incubated for about 15 min at room temperature.

Figure 5:
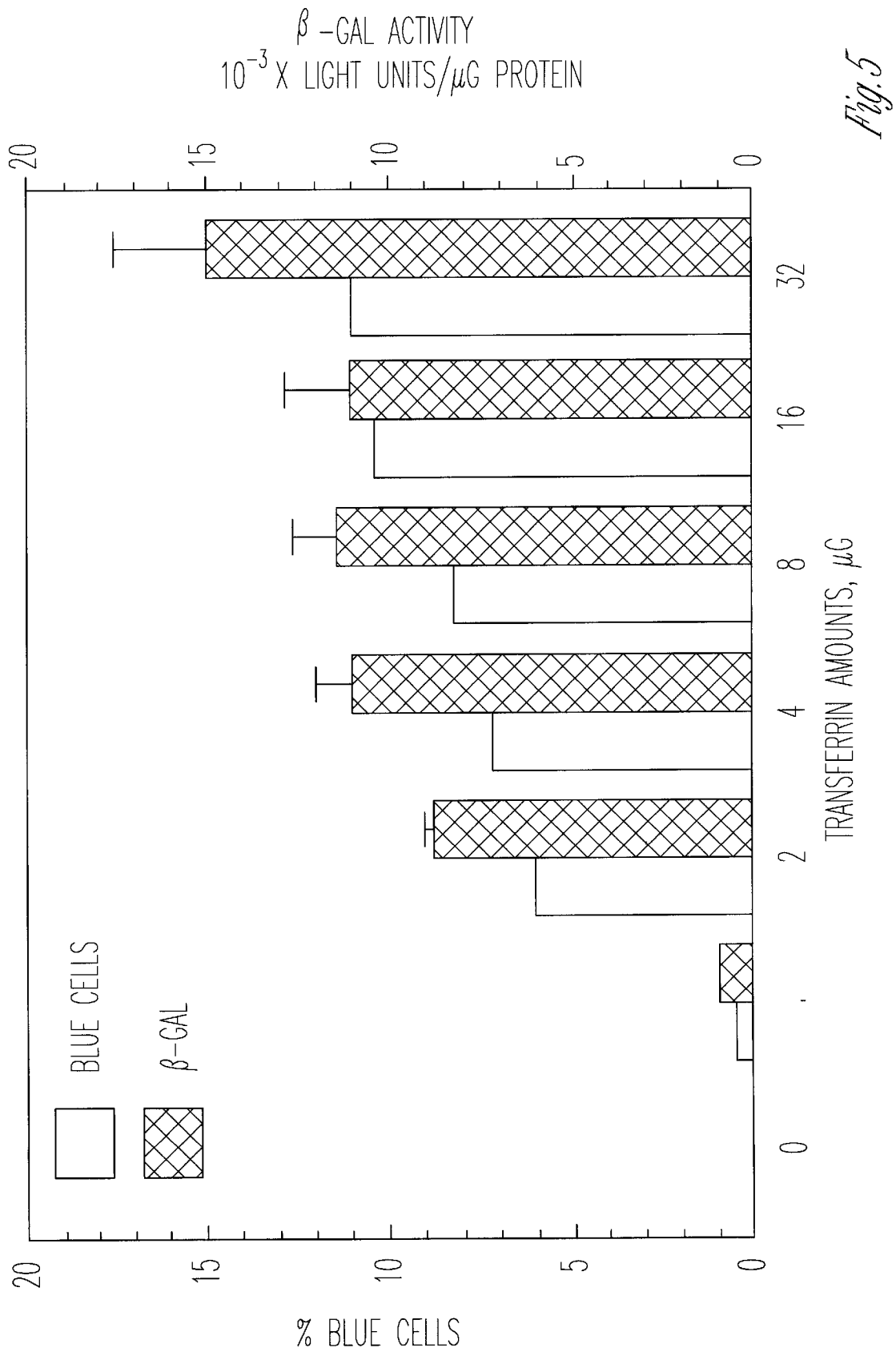
FIG. 5 is a graph of β-galactosidase activity and % blue cells as a function of concentration of transferrin illustrating transferrin enhancement of transfection efficiency of "lipofectin"—mediated gene (pCMVlacZ) transfer.
Figure 6:
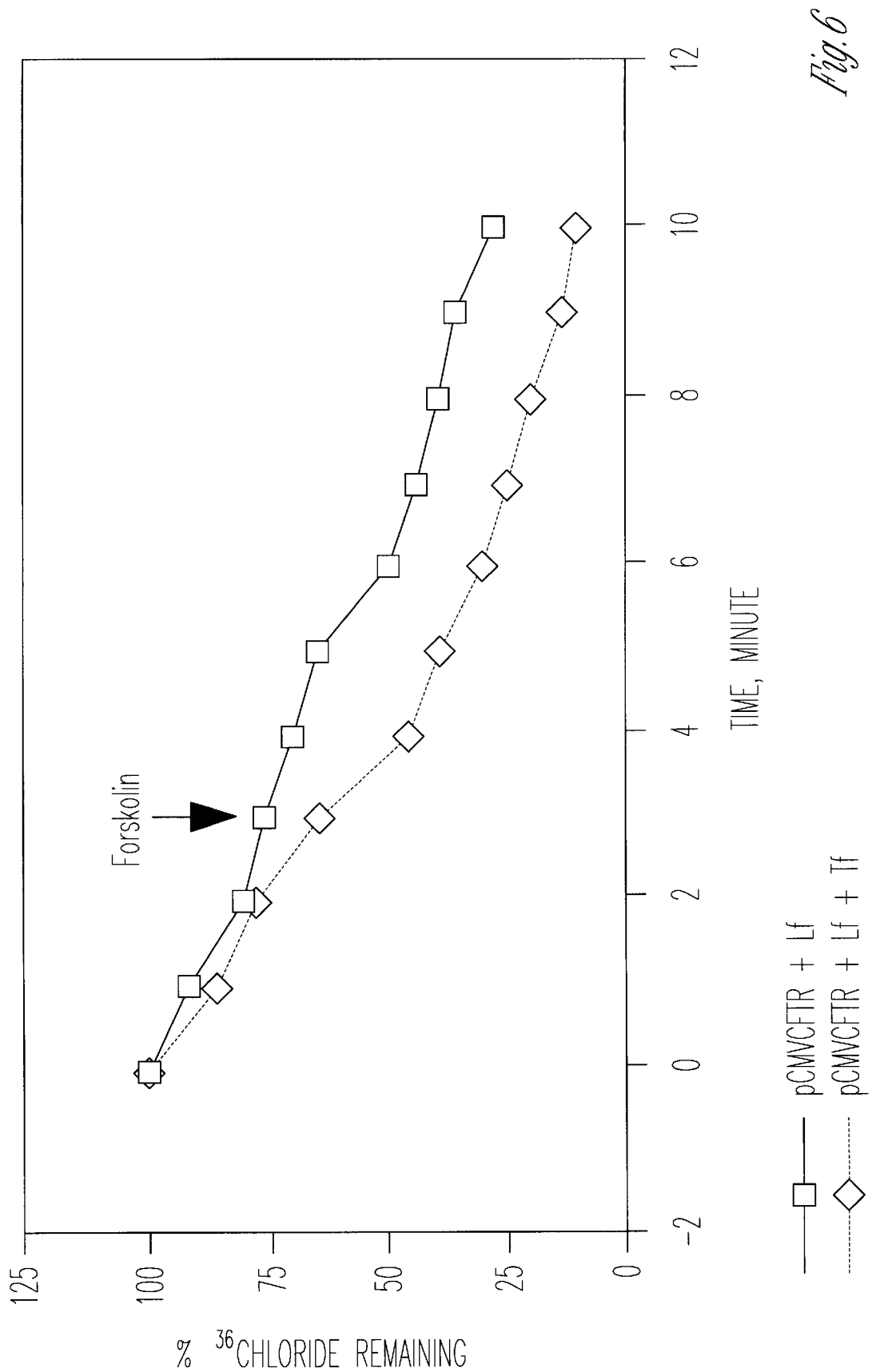
FIG. 6 is a graph illustrating the correction of the chloride ion efflux defect in CFT1 cells. Percent $^{36}$Cl-remaining is plotted as a function of time. In the graph, cells transfected with transferrin, "lipofectin" and pCMVCFTR are indicated by an open diamond (◇) and cells transfected with "lipofectin" and the DNA are indicated by open squares (□). In a separate experiment, the results of which are not shown, the same results as found for transfection with pCMVlacZ plus "lipofectin" were found for CFT1 cells without transfection, CFTI cells transfected with transferrin DNA and "lipofectin" (added in that order) and CFT1 cells transfected with transferrin plus DNA.

The transfected cells were further cultured for 2–3 days before being fixed in glutaraldehyde and then developed with X-gal for 2–3 days. The transfection efficiency (% blue cells) was dependent on transferrin concentration (μg/0.5 mL transfection solution); 0 μg, 0.1%; 1 μg, 0.46%; 2 μg, 5.5%; 4 μg, 7%; 8 μg, 8%; 16 μg, 10%; and 32 μg, 11%. The β-galactosidase activities measured by the Lumigal method also followed the same trend (see FIG. 5). Using the protocol that yielded the highest transfection efficiency to deliver pCMVlacZ to CFT1 cells grown in 35 mm dishes, a 33% transfection efficiency was obtained. CFT1 cells transfected with pCMVCFTR using this protocol exhibited a greater rate of $^{36}$Cl$^-$ effux than CFT1 cells transfected by "lipofectin" without transferrin or CFT1 cells without transfection (see FIG. 6). These results indicate that the transferrin-facilitated CFTR gene transfer mediated by liposome can correct the chloride transport abnormality of CF airway epithelial cells. Significant correction of the chloride transport abnormality was observed when insulin or cholera toxin were employed for transfection with "lipofectin". (See FIG. 7.)

METHODS

Transfection Protocol and Measurement of Transfection Efficiency:

The confluent CFT1 cells grown in a 48-well plate were exposed overnight to a transfection solution (0.5 mL), which contained 3 μg "lipofectin", 1.5 μg DNA, and 1–32 μg transferrin. The transfected cells were then cultured in F-12 medium supplemented with 7 different hormones and growth factors for 2–3 days. Then, cells in 2 wells were fixed in 4% paraformaldehyde at 4° C. for 10 min and exposed to X-gal for 2–3 days. The transfection efficiency was determined by the number of blue cells per 100 cells counted under a phase contrast microscope. Cells in 3 other wells were recovered by trypsinization and their homogenates were measured for β-galactosidase activities by the Lumigal method (Beale et al. (1992) supra. The data were expressed as light units/μg protein. See FIG. 5.

$^{36}$Cl$^{31}$ Efflux Assay:

CFT1 cells were grown to confluence in a 6-well plate. Cells in one well were treated with "lipofectin" and pCMVCFTR plus transferrin and cells in 2 other wells were treated with "lipofectin" and pCMVlacZ plus transferrin as described above. The first two wells were measured for $^{36}$Cl$^-$ efflux and the third well was fixed, treated with X-gal, and measured for % blue cells. The first 2 wells were loaded with 5–10 μCi of $^{31}$Cl$^-$, which was followed by a quick rinse with Cl$^-$ free medium. Then, 1 mL aliquots of isotope-free and Cl$^-$ free medium plus 0.1 mM amiloride was added and removed at 1 min intervals for up to 10 min. At the 3 min time point, 10 μM forskolin was added to assess cAMP-mediated Cl$^-$ permeability. At the end of 10 min the cell-associated isotope was measured in 0.1% SDS extract of the cells. The data were analyzed by plotting the percentage of $^{36}Cl^-$ remaining as a function of time. See FIG. 6.

Transfection Employing $^{36}Cl^-$ Insulin or Cholera Toxin

Employing 6 mL of transfection solution which contains 36 µg "lipofectin" plus 380 µg transferrin, 0.2 µg insulin, or 160 µg cholera toxin to deliver 18 µg pCMVCFTR to confluent CFT1 cells in each well of 6×35 mm plate, significant correction of the chloride transport abnormality was observed (FIG. 7). In a contemporaneous experiment, employing identical protocol to deliver 18 µg pCMVlacZ to CFT1 cells resulted in significant numbers of cells stained blue, i.e. "lipofectin", 0.5%; "lipofectin"+transferrin, 33%; "lipofectin"+insulin, 13%; and "lipofectin"+cholera toxin, 31%. These results demonstrate that it is feasible to restore the cAMP-dependent chloride conductance in CF airway epithelial cells using a wild type CFTR cDNA and the transfection vectors composed of receptors and a cationic liposome.

EXAMPLE 3

Liposome Mediated Transfection Facilitated by Insulin and Cholera Toxin.

Figure 8A:
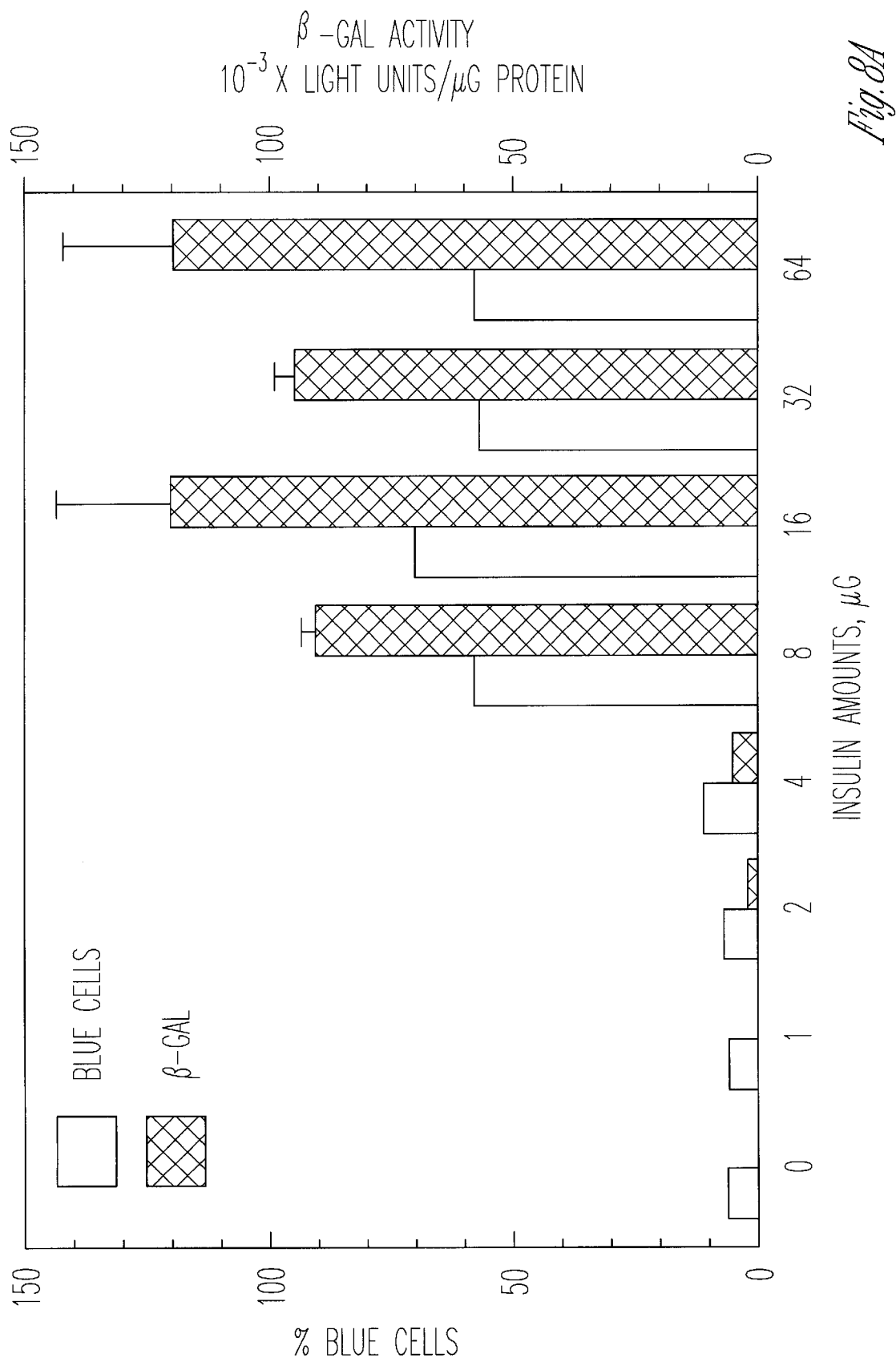
FIGS. 8a and 8b are graphs illustrating transfection efficiency of pCMVlacZ into HeLa cells or CFT1 cells, respectively, as a function of increasing amounts of insulin. The transfection agent is insulin plus "lipofectin".
Figure 8B:
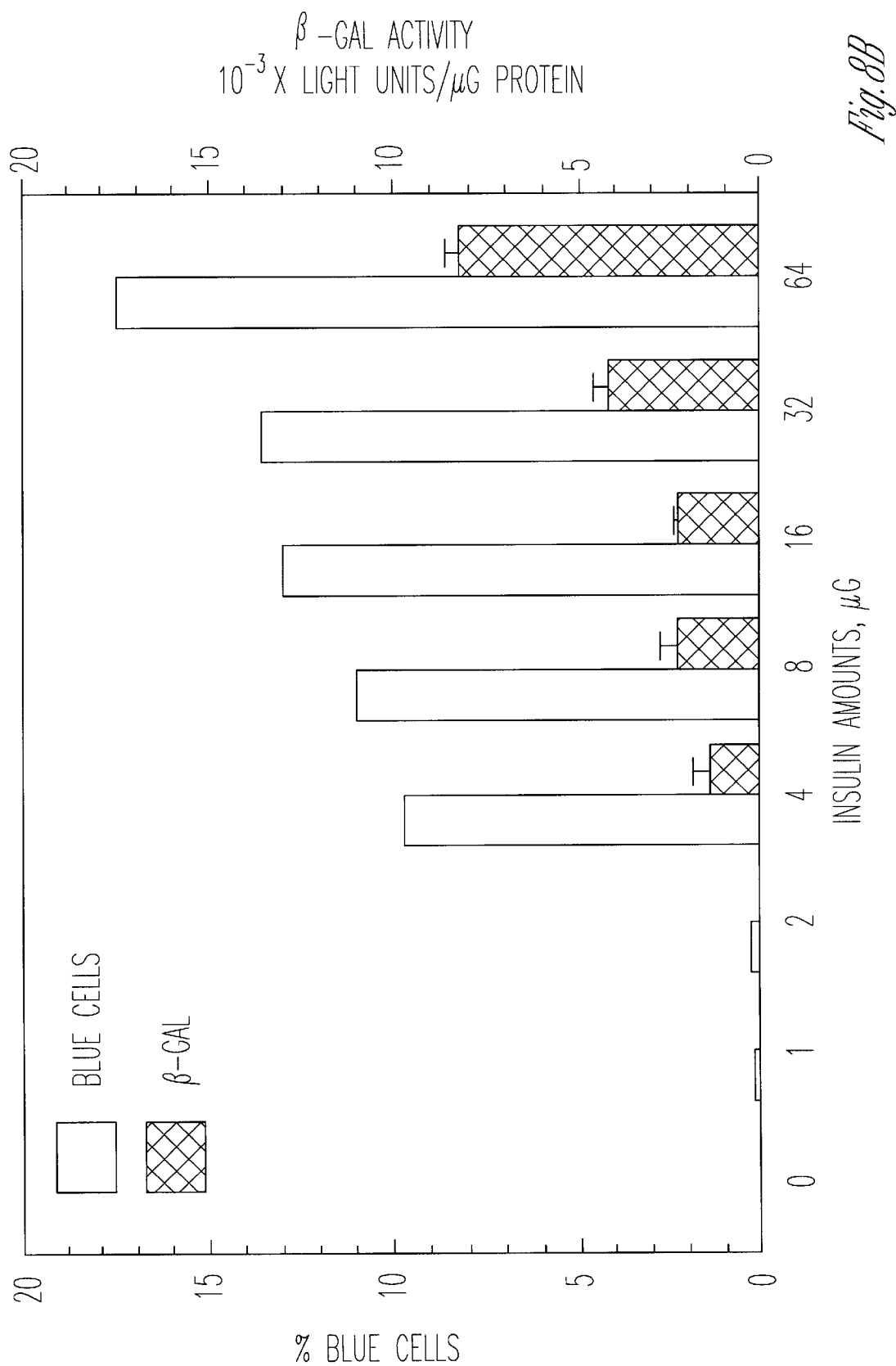
Figure 9A:
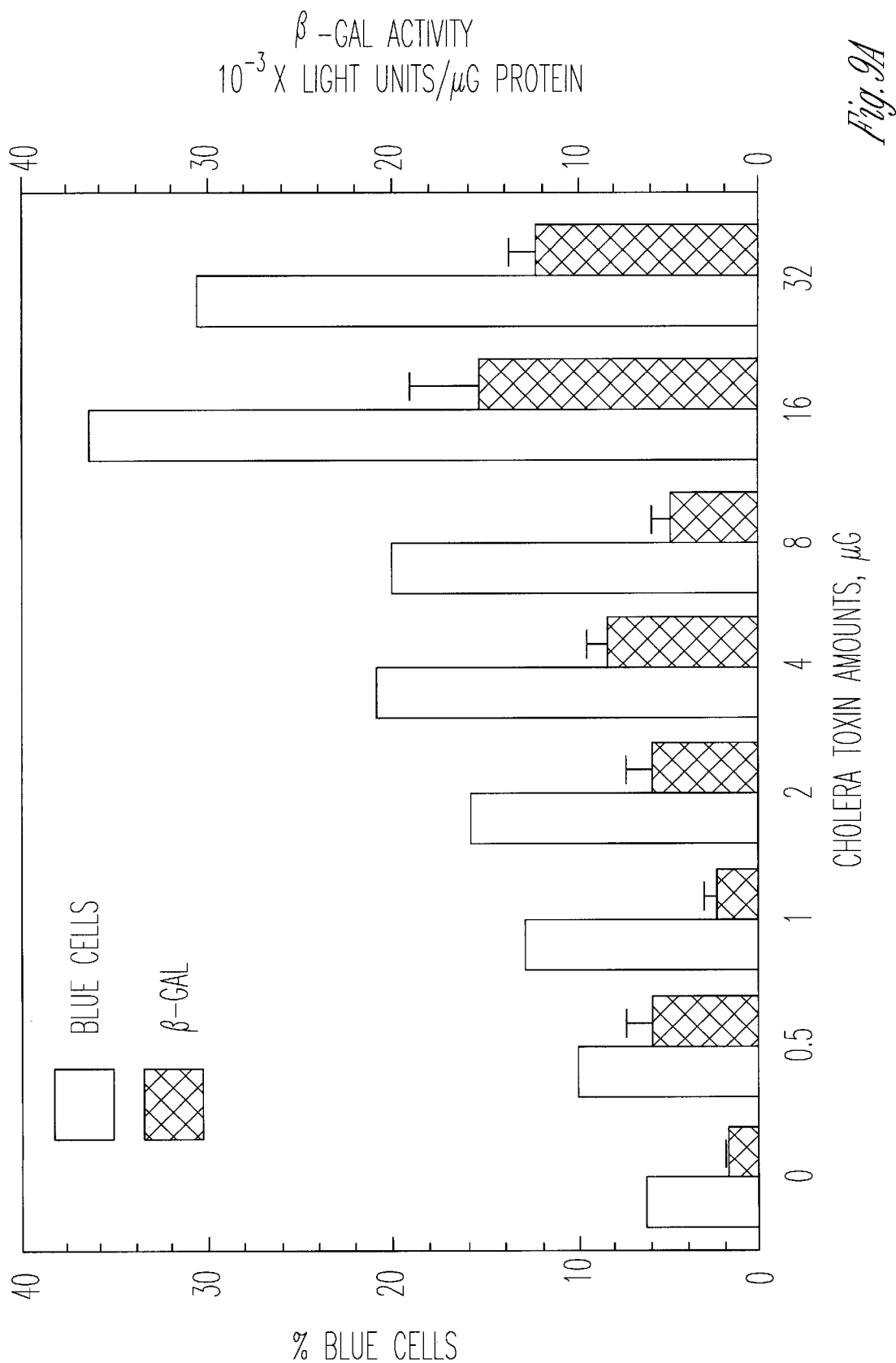
FIGS. 9a and 9b are graphs illustrating transfection efficiency of pCMVlacZ into HeLa or CFT1 cells, respectively, as a function of cholera toxin concentration. The transfection agent is cholera toxin plus "lipofectin".
Figure 9B:
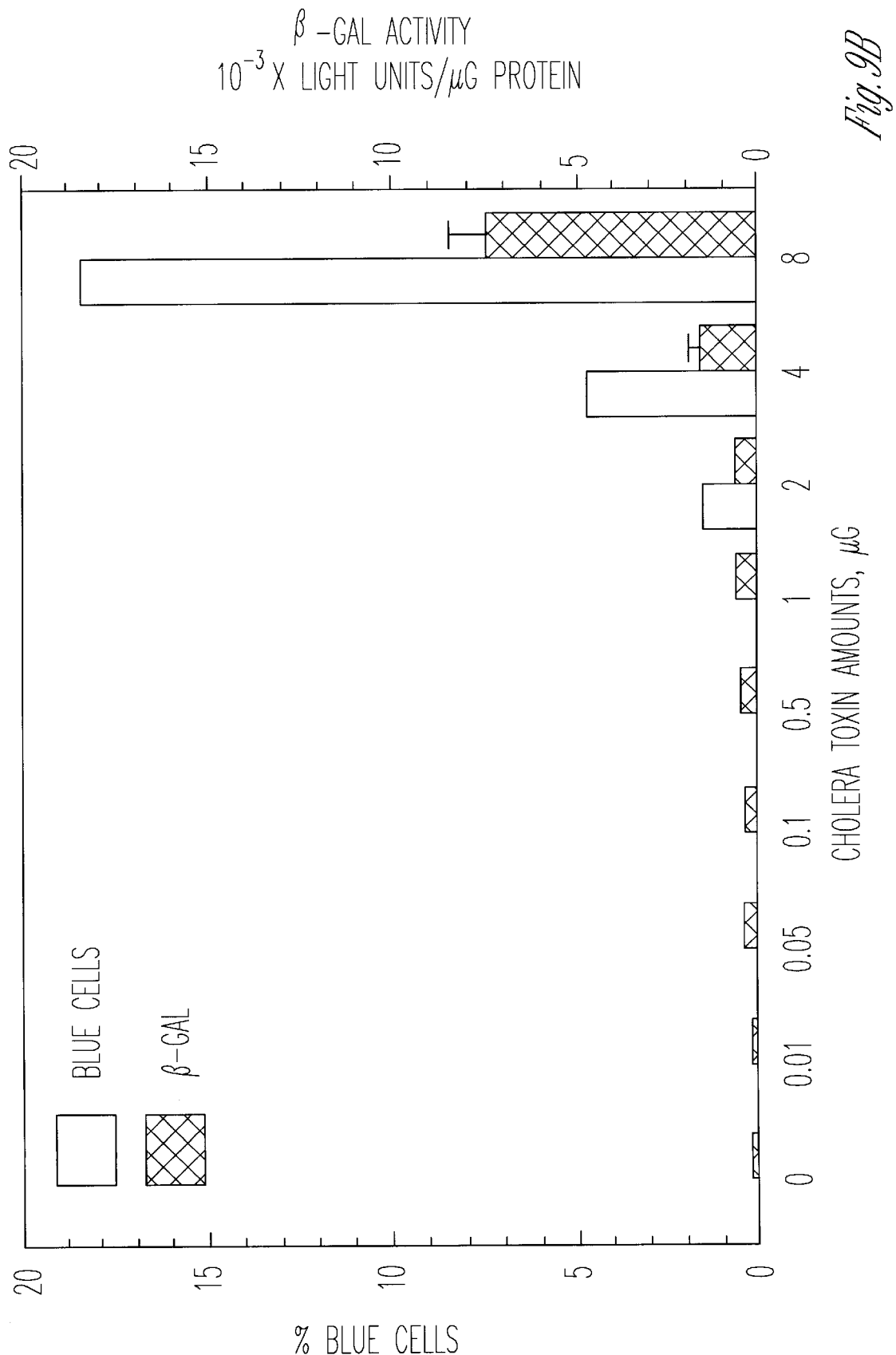

Transfection solutions were prepared as described in Example 1 wherein the receptor ligand was insulin or cholera toxin. FIGS. 8a and 8b show the insulin concentration-dependent transfection efficiency in HeLa cells and CFT1 cells, respectively. FIGS. 9a and 9b show the cholera toxin concentration-dependent transfection efficiency in HeLa cells and CFT1 cells, respectively. Transfection protocols were performed as in Example 1 for HeLa cells and as in Example 2 for CFT1 cells.

Transfection efficiency did not increase when CFT1 cells were transfected with a solution containing a mixture of the three different ligands (transferrin, insulin and cholera toxin). This suggests interference of gene transfection of one receptor ligand by another.

EXAMPLE 4

Components of Human Serum that Facilitate Gene Transfer Mediated by "Lipofectin"

Figure 10:
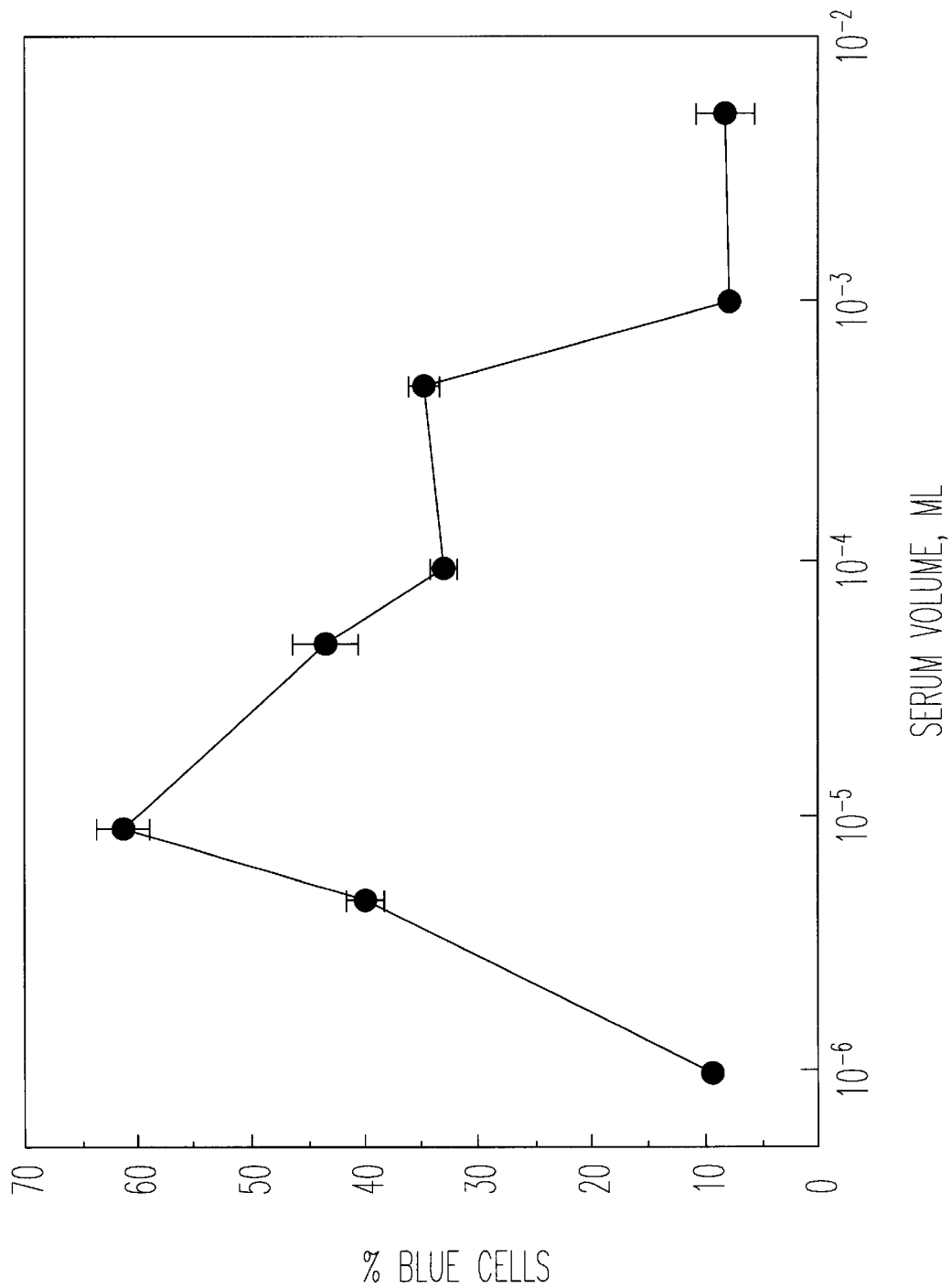
FIG. 10 is a graph illustrating transfection efficiency of a "lipofectin" transfection of pCMVlacZ into HeLa cells as a function of serum volume used in place of the receptor ligand.

The transferrin concentration in human serum is around 2.2–3.7 mg/mL. High transfection efficiency was expected by using 5–10 µL of serum in place of the transferrin receptor ligand. Only marginal transfection efficiency was observed, however, suggesting interference of transferrin-facilitated gene transfection by other human serum components. Maximal gene transfer efficiency was obtained when 0.01 µL of serum was used in place of transferrin in the protocol of Example 1 (FIG. 10).

Figure 11A:
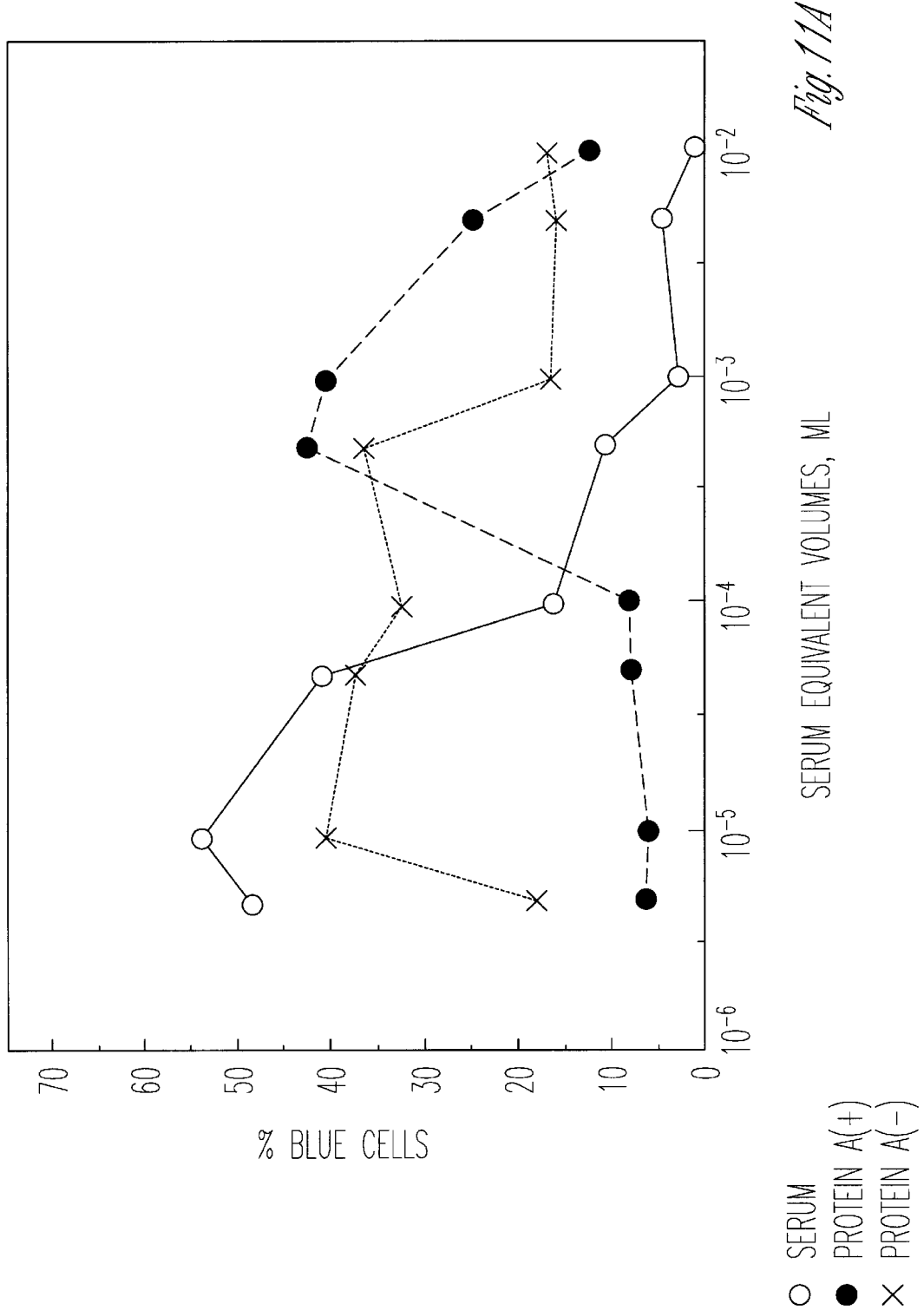
FIGS. 11a and 11b are graphs illustrating transfection efficiency of a "lipofectin" transfection of pCMVlacZ into HeLa cells in which protein A fractions or con A fractions, respectively, are used to replace receptor ligand.
Figure 11B:
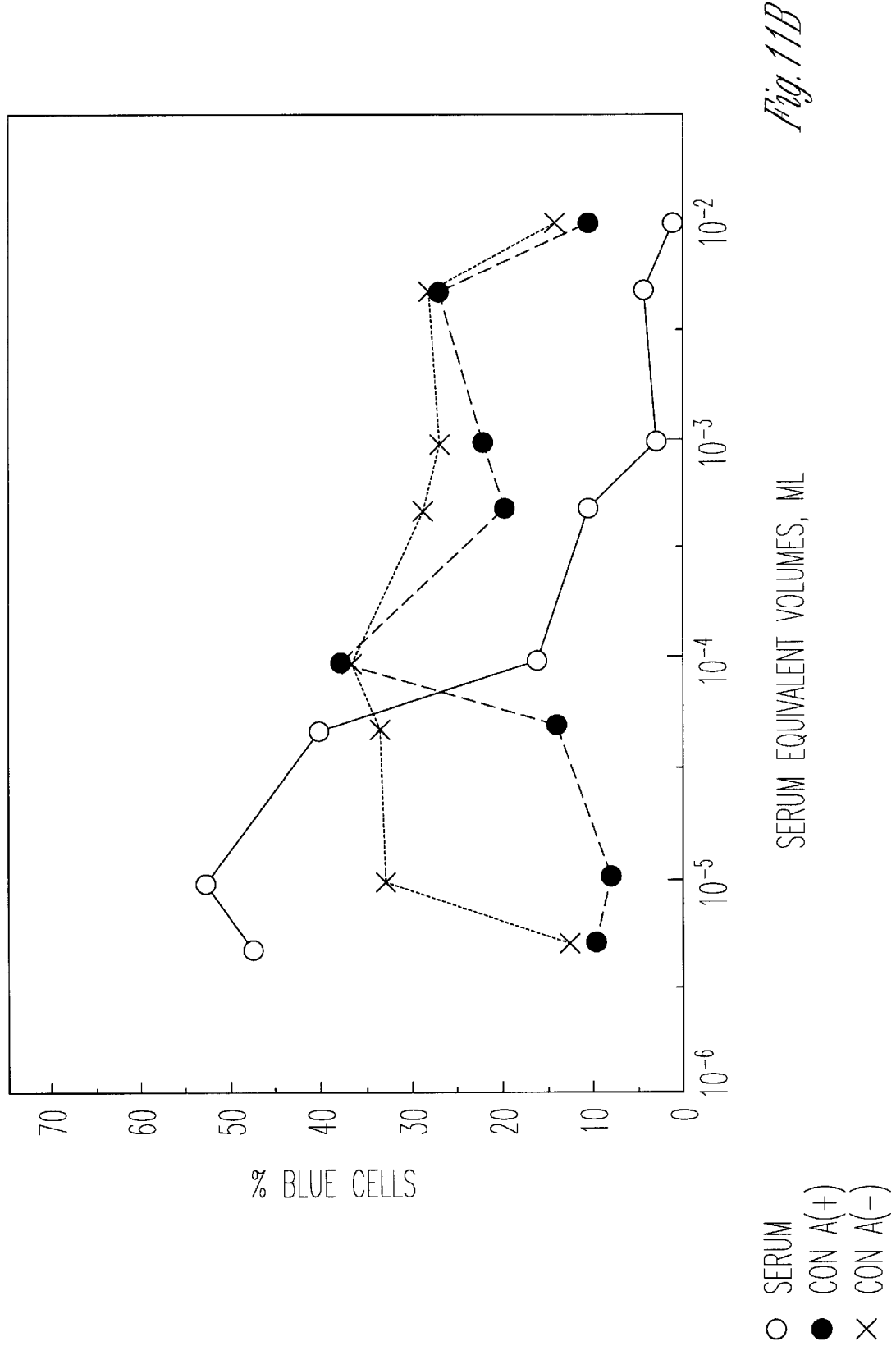

To characterize different serum components which produce high transfection efficiency, a human serum sample was fractionated by protein A-column into IgG-depleted (protein A-:run-through) and IgG-enriched (protein A+: bound and recovered by low pH) fractions. The same serum sample was also fractionated by concanavalin A-column into run-through or Con A-fraction, which contains proteins and mannose-free glycoproteins, and the fraction recovered from Con A, which contains mannose-bound (Con A+) glycoproteins. The transfection efficiencies of protein A fractions are shown in FIG. 11a and Con A fractions in FIG. 11b.

The component(s) responsible for the high transfection efficiency found with 0.01 µl serum appear to be present in protein A- and Con A- fractions but not in the other two fractions. These results indicate that some IgG's and mannose-containing glycoproteins can efficiently facilitate "lipofectin"-mediated gene transfer. Since low transfection efficiency was found using an amount of the protein A– fraction which contained 11–37 µg of transferrin (this concentration of transferrin should yield >80% transfection efficiency), the serum components which interfere with the transferrin-facilitated gene transfer are present substantially in protein A– but not in Con A+ fraction.

Figure 12:
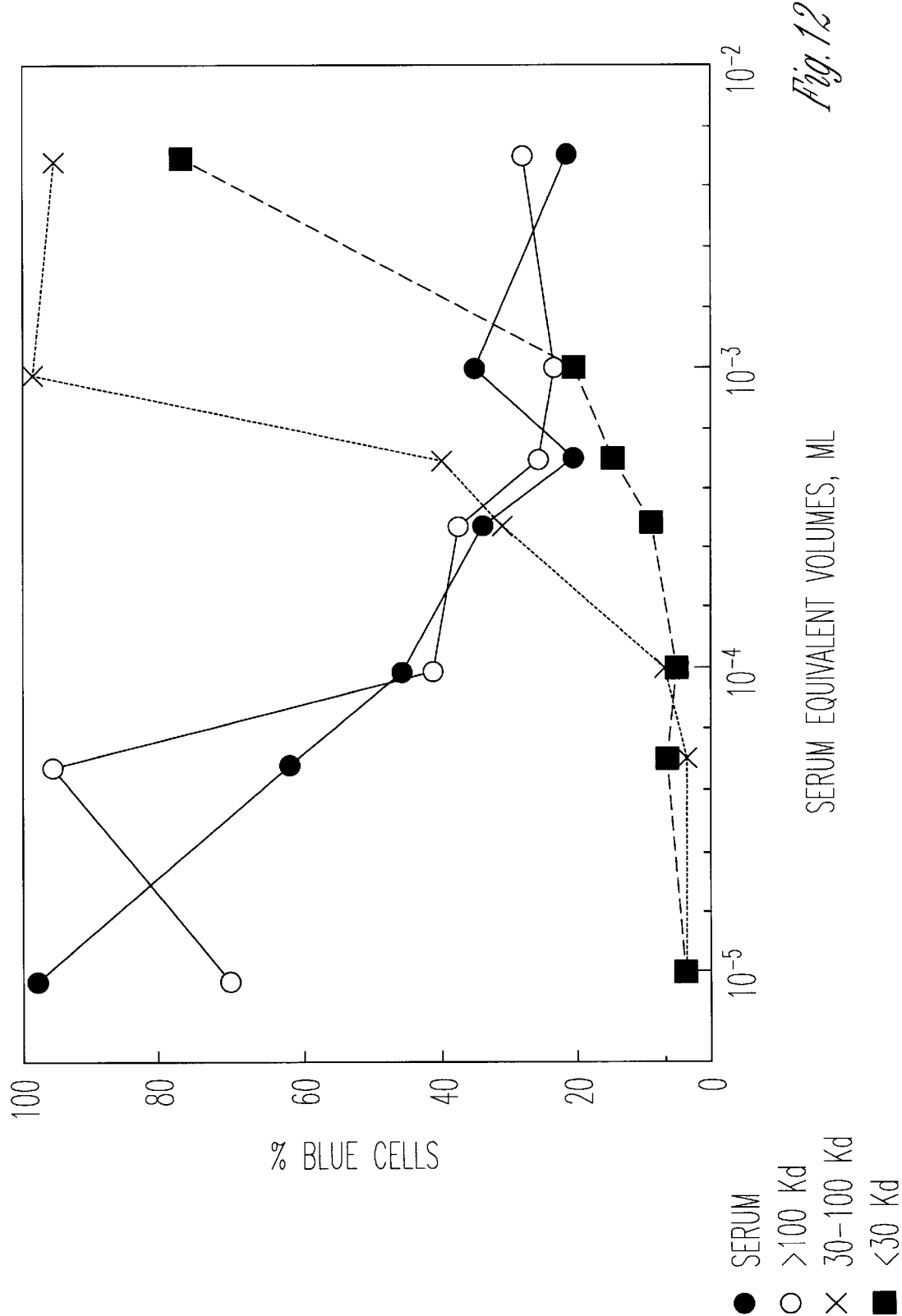
FIG. 12 is a graph illustrating transfection efficiency of a "lipofectin" transfection using size-fractionated serum samples to replace the receptor ligand.

Serum samples were also fractionated according to size using centrifugation filters with MW cut-off of 100 and 30 Kd. As shown in FIG. 12, the component(s) responsible for the high transfection efficiency obtained with 0.01 µl serum appear to have MW greater than 100 Kd. Both the 30–100 Kd and <30 Kd fractions contain compounds which yield high transfection efficiency. Transferrin, which has a MW of 89 Kd, is at least in part responsible for the high-efficiency gene transfer exhibited by the 30–100 Kd fraction. In addition, compounds which interfere with the Tf-facilitated gene transfer were present in the >100 Kd and also in <30 Kd fractions.

TABLE 1

Transferrin and Lipofection-Directed Gene Transfer to Hela Cells: Gene Transfer Efficiency as a Function of Transfection Times (0.5–24 h).

A detailed experimental protocol is described in the Examples. At the end of a 48-hour culture period after transfection with the agent prepared from 16 µg transferrin, 3µg "lipofectin", and 1.5 µg pCMVlacZ, lysates of the cells in 3 wells were measured separately for β-galactosidase activity by the Lumigal method (Beale et al., 1992). β-Galactosidase activity was expressed as light units (mean ±S.E.M.) per tg protein. Hela cells in 3 other wells were stained with X-gal and % of blue cells measured.

| | Transfection with Transferrin-Lipofectin | | Transfection with Lipofectin | |
|---|---|---|---|---|
| Time (h) | β-Galactosidase Activity (Light Units/ µg protein) | Blue Cells (%) | β-Galactosidase Activity (Light Units/ µg protein) | Blue Cells (%) * |
| 0.5 | 2157 ± 144 | 0.9 | 616 ± 32 | 0.6 |
| 1.0 | 4976 ± 357 | 30.4 | 353 ± 17 | 1.2 |
| 3.0 | 10113 ± 402 | 90.0 | 600 ± 210 | 3.1 |
| 5.0 | 25011 ± 1979 | 97.1 | 180 ± 71 | 3.3 |
| 6.0 | 26350 ± 3535 | 99.0 | 414 ± 17 | 3.8 |
| 24.0 | 33769 ± 5733 | 100.0 | 522 ± 138 | 4.0 |

* < 0.01% blue cells were found when the cells were treated with 1.5 µg DNA or DNA plus 32 µg of transferrin.

TABLE 2

Transferrin and Lipofectin-Directed Gene to Hela Cells: Gene Transfer Efficiency as a Function the Amounts (1–32 µg) of Transferrin.

Transfection solution (500 µL) contained 3 µg of "lipofectin", 1.5 µg of pCMVlacZ, and varying amounts of transferring indicated. The transfection time was 18 hours. Detailed experimental protocol is described in the Examples and Table 1.

| Transferrin (μg) | β-Galactosidase Activity (Light Units/μg Protein) | Blue Cells (%) |
|---|---|---|
| 0 | 1923 ± 90 | 3.1 |
| 1 | 1600 ± 95 | 4.3 |
| 2 | 2333 ± 398 | 6.5 |
| 3 | 8210 ± 2770 | 36.0 |
| 4 | 19163 ± 6283 | 86.0 |
| 8 | 86143 ± 12261 | 97.0 |
| 16 | 235920 ± 41472 | 98.0 |
| 32 | 187393 ± 10635 | 98.2* |

*Transfection efficiency, which varied from experiment to experiment, was between 55 and 100%. This variation may be attributable to different batches of reagents.

TABLE 3

Expression of β-Galactosidase in Hela Cells 100% Transfected with Transferrin, Lipofectin and pCMVlacZ (F0) and in the Transfected Cells of Six Consecutive Passages (F1 to F6).

The transfection solution contained 3.0 μg of lipofectin, 16 μg of transferrin, and 1.5 μg of DNA. Cells transfected with "lipofectin" plus DNA, but without transferrin served as the control. Transfection time was 18 h. The experimental protocol is described in the Examples and FIG. 1.

| HeLa Cells (Passages) | Transfection with Transferrin-Lipofectin | | Transfection with Lipofectin | |
|---|---|---|---|---|
| | β-Galactosidase Activity (Light Units/ μg protein) | Blue Cells (%) | β-Galactosidase Activity (Light Units/ μg protein) | Blue Cells (%) |
| F0 | 87546 ± 15140 | 99.8 | 1204 ± 94 | 3.0 |
| F1 | 15233 ± 996 | 69.6 | 460 ± 31 | 0.54 |
| F2 | 5981 ± 950 | 12.3 | 431 ± 37 | 0.23 |
| F3 | 3325 ± 507 | 6.3 | 362 ± 59 | 0.02 |
| F4 | 1450 ± 217 | 1.6 | 120 ± 43 | <0.01 |
| F5 | 550 ± 128 | 0.4 | 322 ± 16 | <0.01 |
| F6 | 240 ± 27 | <0.01 | 129 ± 61 | <0.01 |

TABLE 4

Transferrin-Enhanced pCMVlacZ Transfection Efficiency in HeLa Cells Using Different Cationic Liposome A detailed experimental protocol is described in Table 1 and FIG. 1. The amounts of transferrin and the four different cationic liposomes used were: transferrin, 32 μg; "lipofectin", 3 μg; "lipofectace" 4.2 μg; "lipofectamine" 4 μg; and DC-cholesterol, 4 nmoles.

| Liposome | Transfection with Transferrin-Liposome | | Transfection with Liposome | |
|---|---|---|---|---|
| | β-Galactosidase Activity (Light Units/ μg protein) | Blue Cells (%) | β-Galactosidase Activity (Light Units/ μg protein) | Blue Cells (%) |
| "Lipofectin" | 20,047 ± 3752 | 55 | 1,387 ± 61 | 5.5 |
| "Lipofectace" | 6,428 ± 829 | 35 | 273 ± 59 | 2.7 |
| "Lipofectamine" | 1,133 ± 49 | 7.1 | 796 ± 125 | 7.9 |
| DC-Cholesterol | 884 ± 107 | 10 | 379 ± 30 | 4.2 |

What is claimed is:

1. A method for intracellular delivery of a polynucleotide comprising:
   (a) first combining a non-viral receptor ligand and a cationic lipid to form a mixture, so that said ligand and lipid become associated although not covalently bound; and thereafter
   (b) adding to said mixture a polynucleotide, so that said polynucleotide becomes associated with said lipid to form a molecular mixture; and
   (c) introducing said molecular mixture to a cell, wherein said molecular mixture enhances the delivery of said polynucleotide to said cell.

2. The method of claim 1 further comprising the step of: incubating said mixture prior to addition of the polynucleotide.

3. The method of claim 1 further comprising the step of: incubating said molecular mixture prior to introduction of said molecular mixture to said cell.

4. The method of claim 1 wherein said cationic lipid is in a liposome formulation with a neutral lipid to form a cationic liposome formulation.

5. The method of claim 4 wherein said neutral lipid is dioleoyl phosphatidylethanolamine.

6. The method of claim 4 wherein said liposome formulation is a formulation of N-[1-(2,3-dioleyloxy)propyl]-N,N,N-trimethyl and dioleoyl phosphatidylethanolamine.

7. The method of claim 4 wherein said liposome formulation is a formulation of 2,3-dioleyloxy-N-[2(spermine carboxamido)ethyl]-N,N-dimethyl-1-propanamintrumtrifluoroacetate and dioleoyl phoshalidylethanolamine.

8. The method of claim 4 wherein said formulation has 2,3-dioleyloxy-N-[2(spermine carboxamido)ethyl]-N,N-dimethyl-1-propanamintrumtrifluoroacetate and dioleoyl phoshalidylethanolamine.

9. The method of claim 4 wherein said liposome formulation is a formulation of N,N',N",N"'-tetrapalmetylspermine and dioleoyl phosphatidylethanolamine.

10. The method of claim 1 wherein said cationic lipid is selected from the group consisting of:
    N-[1-(2,3-dioleyloxy)propyl]-N,N,N-trimethyl, dimethyl dioctadecylammonimum bromide; DOSPA; DL-1,2-dioleoyl-3-dimethyl-aminopropyl-B-hydroxyethylammonium; DL-1,2-O-dioleyl-3-dimethylaminopropyl-B-hydroxyethylammonium; DL-1-O-oleyl-2-oleoyl-3-dimethylaminopropyl-B-hydroxyethylammonium; DMRIE; DL-1,2-dioleoyl-3-propyl-N,N,N-trimethylammonium; and TM-TPS.

11. The method of claim 1 wherein said receptor ligand is selected from the group consisting of:
    transferrin, insulin, and cholera toxin.

12. The method of claim 1 wherein said polynucleotide is a deoxyribonucleic acid.

13. The method of claim 1 wherein said polynucleotide is a ribonucleic acid.

14. The method of claim 1 wherein said polynucleotide encodes a gene product.

15. The method of claim 1 wherein said cell is in vitro.

16. The method of claim 1 wherein said cell is in vivo.

17. The method of claim 1 wherein said cell is an animal cell.

18. A method for intracellular delivery of a naked nucleotide sequence without the use of a vector comprising:
    (a) first combining a human protein receptor ligand and a cationic lipid to form a mixture, so that said ligand and lipid become associated although not covalently bound; and thereafter (b) adding to said mixture a naked nucleotide molecule to be delivered to a cell so that said nucleotide molecule becomes associated with said lipid to form a nucleotide mixture, and thereafter (c) introducing said nucleotide mixture to a cell, wherein said nucleotide mixture enhances the delivery of said molecule to said cell.

19. A method for intracellular delivery of a polynucleotide comprising:

(a) first combining a transferrin receptor ligand and a cationic lipid to form a mixture, so that said ligand and lipid become associated although not covalently bound; and thereafter (b) adding to said mixture a polynucleotide to be delivered to a cell to form a molecular mixture; and thereafter (c) introducing said molecular mixture to a cell, wherein said molecular mixture enhances the delivery of said polynucleotide to said cell.

* * * * *